(12) United States Patent
Brenchley et al.

(10) Patent No.: US 8,017,781 B2
(45) Date of Patent: Sep. 13, 2011

(54) AZAINDAZOLES USEFUL AS INHIBITORS OF KINASES

(75) Inventors: Guy Brenchley, Grove Wantage (GB); Jean-Damien Charrier, Grove Wantage (GB); Steven Durrant, Abingdon (GB); Ronald Knegtel, Abingdon (GB); Sharn Ramaya, Burghfield Common (GB); Shazia Sadiq, Oxford (GB); Jingrong Cao, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1230 days.

(21) Appl. No.: 11/600,311

(22) Filed: Nov. 15, 2006

(65) Prior Publication Data
US 2007/0179177 A1    Aug. 2, 2007

Related U.S. Application Data

(60) Provisional application No. 60/737,105, filed on Nov. 15, 2005.

(51) Int. Cl.
*A61K 31/437* (2006.01)
*C07D 471/04* (2006.01)
(52) U.S. Cl. ........................ 546/119; 514/303
(58) Field of Classification Search .................. 546/119; 514/303
See application file for complete search history.

(56) References Cited

U.S. PATENT DOCUMENTS

| | | | |
|---|---|---|---|
| 5,538,843 A | 7/1996 | Hioki et al. | |
| 5,633,232 A | 5/1997 | Matsuo et al. | |
| 5,654,400 A | 8/1997 | Matsuo et al. | |
| 5,663,346 A | 9/1997 | Buzzetti et al. | |
| 5,804,585 A | 9/1998 | Verner | |
| 5,837,704 A | 11/1998 | Hargrave et al. | |
| 5,932,737 A | 8/1999 | Itoh et al. | |
| 6,013,655 A | 1/2000 | Verner | |
| 6,025,366 A | 2/2000 | Walsh et al. | |
| 6,110,931 A | 8/2000 | Walsh et al. | |
| 6,309,811 B2 | 10/2001 | Allway et al. | |
| 6,319,660 B1 | 11/2001 | Allway et al. | |
| 6,329,387 B2 | 12/2001 | Verner | |
| 6,455,242 B1 | 9/2002 | Allway et al. | |
| 6,537,999 B2 | 3/2003 | Gangjee | |
| 6,545,014 B2 | 4/2003 | Verner | |
| 6,552,192 B1 | 4/2003 | Hanus et al. | |
| 6,770,645 B2 | 8/2004 | Denton et al. | |
| 6,897,207 B2 | 5/2005 | Cox et al. | |
| 7,468,376 B2 * | 12/2008 | Rosales et al. | 514/303 |
| 2002/0132810 A1 | 9/2002 | Brown et al. | |
| 2004/0023970 A1 | 2/2004 | Bernotas et al. | |
| 2004/0102432 A1 | 5/2004 | Sanganee et al. | |
| 2004/0192653 A1 | 9/2004 | Munson | |
| 2005/0020639 A1 | 1/2005 | Smith et al. | |
| 2005/0026952 A1 | 2/2005 | Mathias | |
| 2005/0137232 A1 | 6/2005 | Bressi et al. | |

FOREIGN PATENT DOCUMENTS

| | | |
|---|---|---|
| JP | 10036375 | 2/1998 |
| WO | WO 9222569 | 12/1992 |
| WO | WO 9522545 | 8/1995 |
| WO | WO 9600226 | 1/1996 |
| WO | WO 9616981 | 6/1996 |
| WO | WO 9739000 | 10/1997 |
| WO | WO 9951234 | 3/1999 |
| WO | WO 9951231 | 10/1999 |
| WO | WO 0043394 | 7/2000 |
| WO | WO 0220484 | 3/2002 |
| WO | WO 02074774 | 9/2002 |
| WO | WO 03000688 | 1/2003 |
| WO | WO 03000690 | 1/2003 |
| WO | WO 03/045949 | 6/2003 |
| WO | WO 2004014920 | 8/2003 |
| WO | WO 2004009600 | 1/2004 |
| WO | WO 2004/014374 | 2/2004 |
| WO | WO 2004/043953 | 5/2004 |
| WO | WO 2004076450 | 9/2004 |
| WO | WO 2004082638 | 9/2004 |
| WO | WO 2004094411 | 11/2004 |
| WO | WO 2004096130 | 11/2004 |
| WO | WO 2005009389 | 2/2005 |
| WO | WO 2005009438 | 2/2005 |
| WO | WO 2005009964 | 2/2005 |
| WO | WO 2005023818 | 3/2005 |
| WO | WO 2005/042525 | 5/2005 |
| WO | WO 2005/085249 | 9/2005 |
| WO | WO 2006/015124 | 2/2006 |

OTHER PUBLICATIONS

Beutner et. al. "Expedient Synthesis of 3-Alkoxymethyl- and 3-Aminomethyl-Pyrazolo[3,4-b]pyridines" Journal of Organic Chemistry 2009, 74, 789-794.*
Chioua et. al. "Synthesis and biological evaluation of 3,6-diamino-1Hpyrazolo[3,4-b]pyridine derivatives as protein kinase inhibitors" Bioorganic & Medicinal Chemistry Letters 2009, 19, 4566-4569.*
Michelotti et. al. "Two classes of p38a MAP kinase inhibitors having a common diphenylether core but exhibiting divergent binding modes" Bioorganic & Medicinal Chemistry Letters 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*

(Continued)

*Primary Examiner* — Janet Andres
*Assistant Examiner* — David K O Dell
(74) *Attorney, Agent, or Firm* — Rocy C. Stewart

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

8 Claims, No Drawings

OTHER PUBLICATIONS

Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*

Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*

Witherington et. al. "5-Aryl-pyrazolo[3,4-b]pyridines: Potent Inhibitors of Glycogen Synthase Kinase-3 (GSK-3)" Bioorganic & Medicinal Chemistry Letters 13 (2003) 1577-1580.*

Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*

Pejcic, M. et. al. "Antibacterial spectra of seven new 3-aminopyrazolo[3,4-b]pyridine" Pharmaceutica Jugoslavica 1977, 27(3), 143-6.*

El-Dean, A.M. Kamal; Atalla, A.A.; Mohamed, T.A.; Geies, A.A., "Synthesis of some Pyrazolopyridine Sulphonamide Derivatives", Zeitschrift fur Naturforschung, Section B: Chemical Sciences, (1991), 46(4), 541-6. .

The International Search Report received in the corresponding PCT Application No. PCT/US2006/044361.

* cited by examiner

SEQUENCE LISTING

```
<160> NUMBER OF SEQ ID NOS: 4

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Lys Lys Ile Ser Asp Glu Leu Met Asp Ala Thr Phe Ala Asp Gln
1               5                   10                  15

Glu Ala Lys

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Lys Met Asp Ala Thr Phe Ala Asp Gln
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Glu Glu Glu Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ser Ser Pro His Gln Ser Glu Asp Glu Glu Glu
1               5                   10
```

US 8,017,781 B2

AZAINDAZOLES USEFUL AS INHIBITORS OF KINASES

CROSS REFERENCE TO RELATED APPLICATIONS

This present application claims benefit, under 35 U.S.C. §119, to U.S. Provisional Application No. 60/737,105, filed Nov. 15, 2005, the entire disclosure of which is incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention.

SEQUENCE LISTING

The instant application contains a Sequence Listing which has been submitted via EFS-Web and is hereby incorporated by reference in its entirety. The ASCII copy, created on Aug. 9, 2010, is named VPI05166.txt and is 1,409 bytes in size.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see Hardie, G and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (eg protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (eg shock, heat shock, ultraviolet radiation, bacterial endotoxin, and $H_2O_2$), cytokines (eg interleukin-1 (IL-1) and tumor necrosis factor alpha (TNF-a), and growth factors (eg granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (Plk) belong to a family of serine/threonine kinases that are highly conserved across the species, ranging from yeast to man (reviewed in Lowery D M et al., *Oncogene* 2005, 24; 248-259). The Plk kinases have multiple roles in cell cycle, including control of entry into and progression through mitosis.

Plk1 is the best characterized of the Plk family members. Plk1 is widely expressed and is most abundant in tissues with a high mitotic index. Protein levels of Plk1 rise and peak in mitosis (Hamanaka, R et al., *J Biol Chem* 1995, 270, 21086-21091). The reported substrates of Plk1 are all molecules that are known to regulate entry and progression through mitosis, and include CDC25C, cyclin B, p53, APC, BRCA2 and the proteasome. Plk1 is upregulated in multiple cancer types and the expression levels correlate with severity of disease (Macmillan, J C et al., *Ann Surg Oncol* 2001, 8, 729-740). Plk1 is an oncogene and can transform NIH-3T3 cells (Smith, M R et al., *Biochem Biophys Res Commun* 1997, 234, 397-405). Depletion or inhibition of Plk1 by siRNA, antisense, microinjection of antibodies, or transfection of a dominant negative construct of Plk1 into cells, reduces proliferation and viability of tumour cells in vitro (Guan, R et al., *Cancer Res* 2005, 65, 2698-2704; Liu, X et al., *Proc Natl Acad Sci USA* 2003, 100, 5789-5794, Fan, Y et al., *World J Gastroenterol* 2005, 11, 4596-4599; Lane, H A et al., *J Cell Biol* 1996, 135, 1701-1713). Tumour cells that have been depleted of Plk1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of Plk1. In vivo knock down of Plk1 by siRNA or the use of dominant negative constructs leads to growth inhibition or regression of tumours in xenograft models.

Plk2 is mainly expressed during the G1 phase of the cell cycle and is localized to the centrosome in interphase cells. Plk2 knockout mice develop normally, are fertile and have normal survival rates, but are around 20% smaller than wild type mice. Cells from knockout animals progress through the cell cycle more slowly than in normal mice (Ma, S et al., *Mol Cell Biol* 2003, 23, 6936-6943). Depletion of Plk2 by siRNA or transfection of kinase inactive mutants into cells blocks centriole duplication. Downregulation of Plk2 also sensitizes tumour cells to taxol and promotes mitotic catastrophe, in part by suppression of the p53 response (Burns T F et al., *Mol Cell Biol* 2003, 23, 5556-5571).

Plk3 is expressed throughout the cell cycle and increases from G1 to mitosis. Expression is upregulated in highly proliferating ovarian tumours and breast cancer and is associated with a worse prognosis (Weichert, W et al., *Br J Cancer* 2004, 90, 815-821; Weichert, W et al., *Virchows Arch* 2005, 446, 442-450). In addition to regulation of mitosis, Plk3 is believed to be involved in Golgi fragmentation during the cell cycle and in the DNA-damage response. Inhibition of Plk3 by dominant negative expression is reported to promote p53-independent apoptosis after DNA damage and suppresses colony formation by tumour cells (Li, Z et al., *J Biol Chem* 2005, 280, 16843-16850.

Plk4 is structurally more diverse from the other Plk family members. Depletion of this kinase causes apoptosis in cancer cells (Li, J et al., *Neoplasia* 2005, 7, 312-323). Plk4 knockout mice arrest at E7.5 with a high fraction of cells in mitosis and partly segregated chromosomes (Hudson, J W et al., *Current Biology* 2001, 11, 441-446).

Molecules of the protein kinase family have been implicated in tumour cell growth, proliferation and survival. Accordingly, there is a great need to develop compounds useful as inhibitors of protein kinases.

Additionally, the evidence implicating the Plk kinases as essential for cell division is strong. Blockade of the cell cycle is a clinically validated approach to inhibiting tumour cell proliferation and viability. It would therefore be desirable to develop compounds that are useful as inhibitors of the Plk family of protein kinases (eg Plk1, Plk2, Plk3 and Plk4), that would inhibit proliferation and reduce viability of tumour cells, particularly as there is a strong medical need to develop new treatments for cancer.

SUMMARY OF THE INVENTION

Compounds of this invention, and pharmaceutically acceptable compositions thereof, are effective as inhibitors of protein kinases. In certain embodiments, these compounds are effective as inhibitors of PLK1 protein kinases. These compounds have the formula I, as defined herein, or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease, a neurodegenerative disease, or an immunologically-mediated disease. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention describes compounds of Formula I:

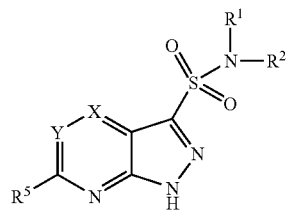

I or a pharmaceutically accepted salt thereof, wherein,
wherein,
$R^1$ is $(L^1)_n$-$Z^1$;
$R^2$ is H or $(L^2)_m$-$Z^2$; or
$R^1$ and $R^2$, together with the nitrogen atom to which they are attached, form a 3-14 membered saturated or partially unsaturated monocyclic or bicyclic heterocyclic ring; said ring is optionally substituted with 0-5 occurrences of $J^R$;
X is $CR^3$ or N;
Y is $CR^4$ or N;
$R^3$ is H, CN, $NO_2$, halo, or $(L^3)_p$-$Z^3$;
$R^4$ is H, CN, $NO_2$, halo, or $(L^4)_q$-$Z^4$;
$R^5$ is H, CN, $NO_2$, halo, $C_{1-6}$aliphatic, or a $C_{1-6}$alkylidene chain wherein up to three methylene units of the chain are optionally and independently replaced by —N(R)—, —O—, —S—, —S(O)—, —S(O)$_2$—, —C(S)—, —C(=NR)—, or —C(O)—; $R^5$ is optionally substituted with 0-3 $J^{R5}$;
each $L^1$, $L^2$, $L^3$, and $L^4$ is independently a $C_{1-6}$alkylidene chain wherein up to three methylene units of the chain are optionally and independently replaced by —N(R)—, —O—, —S—, —S(O)—, —S(O)$_2$—, —C(S)—, —C(=N)R—, or —C(O)—;
$L^1$ is optionally substituted with 0-3 $J^{L1}$;
$L^2$ is optionally substituted with 0-3 $J^{L2}$;
$L^3$ is optionally substituted with 0-3 $J^{L3}$;
$L^4$ is optionally substituted with 0-3 $J^{L4}$;
each $Z^1$, $Z^2$, and $Z^4$ is independently H, $C_{1-6}$ aliphatic, 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur;
$Z^1$ is optionally substituted with 0-5 $J^{Z1}$;
$Z^2$ is optionally substituted with 0-5 $J^{Z2}$;
$Z^4$ is optionally substituted with 0-5 $J^{Z4}$;
$Z^3$ is H, $C_{1-6}$ aliphatic, 3-8-membered saturated, partially unsaturated, or fully unsaturated monocyclic ring having 0-3 heteroatoms independently selected from nitrogen, oxygen, or sulfur; $Z^3$ is optionally substituted with 0-5 $J^{Z3}$;
each $J^{L1}$, $J^{L2}$, $J^{L3}$, and $J^{L4}$ is independently H, $C_{1-6}$ aliphatic, $C_{3-6}$cycloaliphatic, phenyl, —($C_{1-4}$alkyl)-(phenyl), halogen, $NO_2$, CN, $NH_2$, —NH($C_{1-4}$ aliphatic), —N($C_{1-4}$ aliphatic)$_2$, —OH, —O($C_{1-4}$ aliphatic), —O(halo$C_{1-4}$aliphatic), —S($C_{1-4}$ aliphatic), —C(O)OH, —C(O)O($C_{1-4}$ aliphatic), —CONH$_2$, —CONH($C_{1-4}$ aliphatic), —CO( )N($C_{1-4}$ aliphatic)$_2$, —CO($C_{1-4}$ aliphatic) or halo($C_{1-4}$ aliphatic); wherein each of the foregoing aliphatic or phenyl groups is optionally substituted with $C_{1-3}$alkyl, halogen, OH, $OCH_3$, $OCF_3$, $NO_2$, $NH_2$, CN, $NHCH_3$, $SCH_3$, $N(CH_3)_2$, or halo($C_{1-3}$ alkyl);
each $J^R$ is independently H, CN, $NO_2$, halo, phenyl, —($C_{1-4}$ alkyl)-(phenyl), 5-6 membered heteroaryl, 3-8 membered cycloaliphatic, 4-8 membered heterocyclyl, or a $C_{1-6}$alkylidene chain wherein up to three methylene units of the chain are optionally and independently replaced by —N(R)—, —O—, —S—, —S(O)—, —S(O)$_2$—, —C(S)—, —C(=N)R—, or —C(O)—; wherein each of the foregoing groups is optionally substituted with $C_{1-3}$alkyl, halogen, OH, $OCH_3$, $OCF_3$, $NO_2$, $NH_2$, CN, $NHCH_3$, $SCH_3$, $N(CH_3)_2$, or halo($C_{1-3}$ alkyl);
each $J^{R5}$, $J^{Z1}$, $J^{Z2}$, $J^{Z3}$, and $J^{Z4}$ is independently H, CN, $NO_2$, halo, or $(X)_r$-M;
X is a $C_{1-6}$alkylidene chain wherein up to three methylene units of the chain are optionally and independently replaced by —NH—, —N($C_{1-6}$aliphatic)-, —O—, —S—, —S(O)—, —S(O)$_2$—, —C(S)—, —C(=NH)—, —C(=N($C_{1-6}$aliphatic))-, or —C(O)—; wherein each of the foregoing aliphatic groups is optionally substituted with $C_{1-3}$alkyl, halogen, OH, $OCH_3$, $OCF_3$, $NO_2$, $NH_2$, CN, $NHCH_3$, $SCH_3$, $N(CH_3)_2$, or halo($C_{1-3}$ alkyl);

M is H, $C_{5-10}$aryl, 5-10 membered heteroaryl, $C_{3-10}$ cycloaliphatic, 4-10 membered heterocyclyl, or $C_{1-6}$aliphatic; wherein M is optionally substituted with 0-5 occurrences of $C_{1-6}$ aliphatic, $C_{3-6}$cycloaliphatic, halogen, —$NO_2$, —CN, —$NH_2$, —NH($C_{1-4}$ aliphatic), —N($C_{1-4}$ aliphatic)$_2$, —OH, —O($C_{1-4}$ aliphatic), —O(halo$C_{1-4}$aliphatic), —S($C_{1-4}$ aliphatic), —C(O)OH, —C(O)O($C_{1-4}$ aliphatic), —C(O)$NH_2$, —C(O)NH($C_{1-4}$ aliphatic), —C(O)N($C_{1-4}$ aliphatic)$_2$, —C(O)($C_{1-4}$ aliphatic), or halo($C_{1-4}$ aliphatic); wherein each of the foregoing aliphatic groups is optionally substituted with $C_{1-3}$alkyl, halogen, OH, $OCH_3$, $OCF_3$, $NO_2$, $NH_2$, CN, $NHCH_3$, $SCH_3$, $N(CH_3)_2$, or halo($C_{1-3}$ alkyl);

R is H, $C_{1-6}$aliphatic, C(=O)($C_{1-6}$aliphatic), —($C_{1-4}$alkyl)-(phenyl), a 3-8-membered saturated, partially unsaturated, or fully unsaturated monocyclic ring having 0-3 heteroatoms independently selected from nitrogen, oxygen, or sulfur; R is optionally substituted with 0-5 occurrences of $C_{1-3}$alkyl, halogen, OH, $OCH_3$, $OCF_3$, $NO_2$, $NH_2$, CN, $NHCH_3$, $SCH_3$, $N(CH_3)_2$, or halo($C_{1-3}$ alkyl);

n, m, p, q, and t are each independently 0 or 1;

provided that when n is 0, $Z^1$ is not H;

when m is 0, $Z^2$ is not H;

when p is 0, $Z^3$ is not H;

when q is 0, $Z^4$ is not H.

In some embodiments, when $R^3$ and $R^5$ are $CH_3$, $R^4$ is H, then $R^1$ and $R^2$ do not join to form

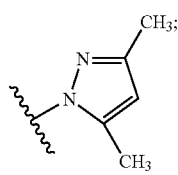

when $R^3$ and $R^5$ are $CH_3$, $R^4$ is H, and $R^2$ is H, then $R^1$ is not H, —NH—N=CH—Ph, —NH—$NH_2$, phenyl, 4-methylphenyl,

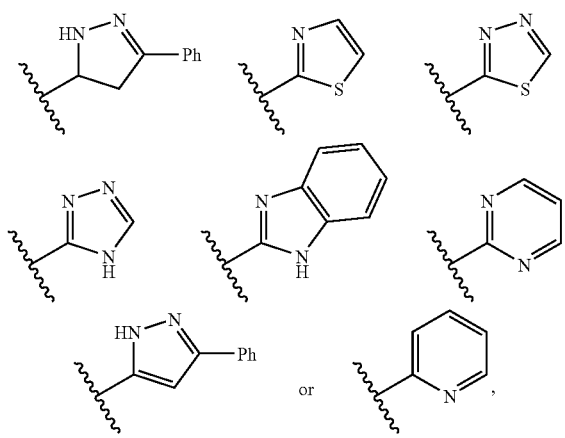

wherein Ph is unsubstituted phenyl.

In some embodiments, $R^5$ cannot be OH.

In other embodiments, $R^4$ cannot be H.

In some embodiments, If n is 0 and Z is cyclohexane, then $J^{Z1}$ is not $(X)_t$-M wherein t is 1, X is —NCO—, and M is 3-pyridyl substituted with —O—(Ph) wherein Ph is a phenyl group optionally substituted or optionally fused to another 5 membered ring.

In other embodiments, $R^1$ and $R^2$ are not both H.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "alkylidene chain" refers to a straight or branched carbon chain that may be fully saturated or have one or more units of unsaturation and has two points of attachment to the rest of the molecule.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound.

Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention.

Unless otherwise indicated, a substituent can freely rotate around any rotatable bonds. For example, a substituent drawn as also represents Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

The following abbreviations are used:

| | |
|---|---|
| HOAc | acetic acid |
| THF | tetrahydrofuran |
| Pd(PPh$_3$)$_4$ | tetrakis(triphenylphosphine)palladium |
| PG | protecting group |
| DMF | dimethylformamide |
| DCM | dichloromethane |
| Ac | acetyl |
| Bu | butyl |
| Et | ethyl |
| DMF | dimethylformamide |
| EtOAc | ethyl acetate |
| DMSO | dimethyl sulfoxide |
| MeCN | acetonitrile |
| TFA | trifluoroacetic acid |
| TCA | trichloroacetic acid |
| ATP | adenosine triphosphate |
| EtOH | ethanol |
| Ph | phenyl |
| Me | methyl |
| Et | ethyl |
| HEPES | 4-(2-hydroxyethyl)-1-piperazineethanesulfonic acid |
| BSA | bovine serum albumin |
| DTT | dithiothreitol |
| NMR | nuclear magnetic resonance |
| HPLC | high performance liquid chromatography |
| LCMS | liquid chromatography-mass spectrometry |
| TLC | thin layer chromatography |
| Rt | retention time |

In some embodiments, X is $CR^3$. In other embodiments, Y is $CR^4$. In some embodiments, X is $CR^3$ and Y is $CR^4$. In other embodiments, only one of X or Y is N.

In some embodiments, $Z^1$ is a 3-8-membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur. In other embodiments, $Z^1$ is a 3-8-membered saturated, partially unsaturated, or fully unsaturated monocyclic ring having 0-3 heteroatoms independently selected from nitrogen, oxygen, or sulfur. In some embodiments, $Z^1$ is a 5-8 membered heterocyclyl, 3-8 membered cycloaliphatic, phenyl, or 5-6 membered heteroaryl.

In some embodiments, $Z^1$ is a 5-6 membered aryl or heteroaryl. In some embodiments, $Z^1$ is a 5-6 membered heteroaryl. In some embodiments, $Z^1$ is pyridyl, pyrimidyl, pyridazinyl, or pyrazinyl. In other embodiments, $Z^1$ is a 5-membered heteroaryl. In yet other embodiments, $Z^1$ is phenyl.

In some embodiments, $Z^1$ is a 4-8 membered heterocyclyl. In some embodiments, $Z^1$ is a 5-6 membered heterocyclyl containing 1-2 heteroatoms selected from O, N, or S. In some embodiments, $Z^1$ is pyrrolidinyl, piperidinyl, pyrazinyl, or morpholinyl.

In other embodiments, $Z^1$ is a 3-8 membered cycloaliphatic.

In some embodiments, n is 0. In other embodiments, n is 1.

In some embodiments of this invention, $L^1$ is a $C_{1-6}$ alkylidene chain. In some embodiments, $L^1$ is —$CH_2$—. In some embodiments, $L^1$ is a $C_{1-6}$ alkylidene chain wherein 1-2 methylene units are replaced with O, N, or S.

In other embodiments, $L^2$ is a $C_{1-6}$ alkylidene chain. In some embodiments, $L^2$ is —$CH_2$—.

In some embodiments, $R^2$ is H.

In other embodiments, $R^3$ is H, CN, $NO_2$, halo, or a $C_{1-6}$alkylidene chain. In some embodiments, $R^3$ is H.

In some embodiments, $R^5$ is H, CN, $NO_2$, halo, or a $C_{1-6}$alkylidene chain. In some embodiments, $R^5$ is H.

In some embodiments, both $R^3$ and $R^5$ are H.

In other embodiments, $R^4$ is H.

In some embodiments, $R^4$ is $(L^4)_q$-$Z^4$. In some embodiments, $Z^4$ is a 3-8-membered saturated, partially unsaturated, or fully unsaturated monocyclic ring having 0-3 heteroatoms independently selected from nitrogen, oxygen, or sulfur. In other embodiments, $Z^4$ is a 5-8 membered heterocyclyl, 3-8 membered cycloaliphatic, phenyl, or 5-6 membered heteroaryl. In some embodiments, $Z^4$ is a 5-6 membered aryl or heteroaryl. In other embodiments, $Z^4$ is a 5-6 membered heteroaryl. In yet other embodiments, $Z^4$ is pyridyl, pyrimidyl, pyridazinyl, or pyrazinyl. In some embodiments, $Z^4$ is a 5-membered heteroaryl. In other embodiments, $Z^4$ is phenyl. In some embodiments, $Z^4$ is H.

In other embodiments, $R^3$, $R^4$, and $R^5$ are H.

In some embodiments, q is 0. In other embodiments, q is 1. In some embodiments, $L^4$ is a $C_{1-6}$ alkylidene chain.

In one embodiment, the invention consists of the following compounds:
In another embodiment the invention consists of the following compounds:
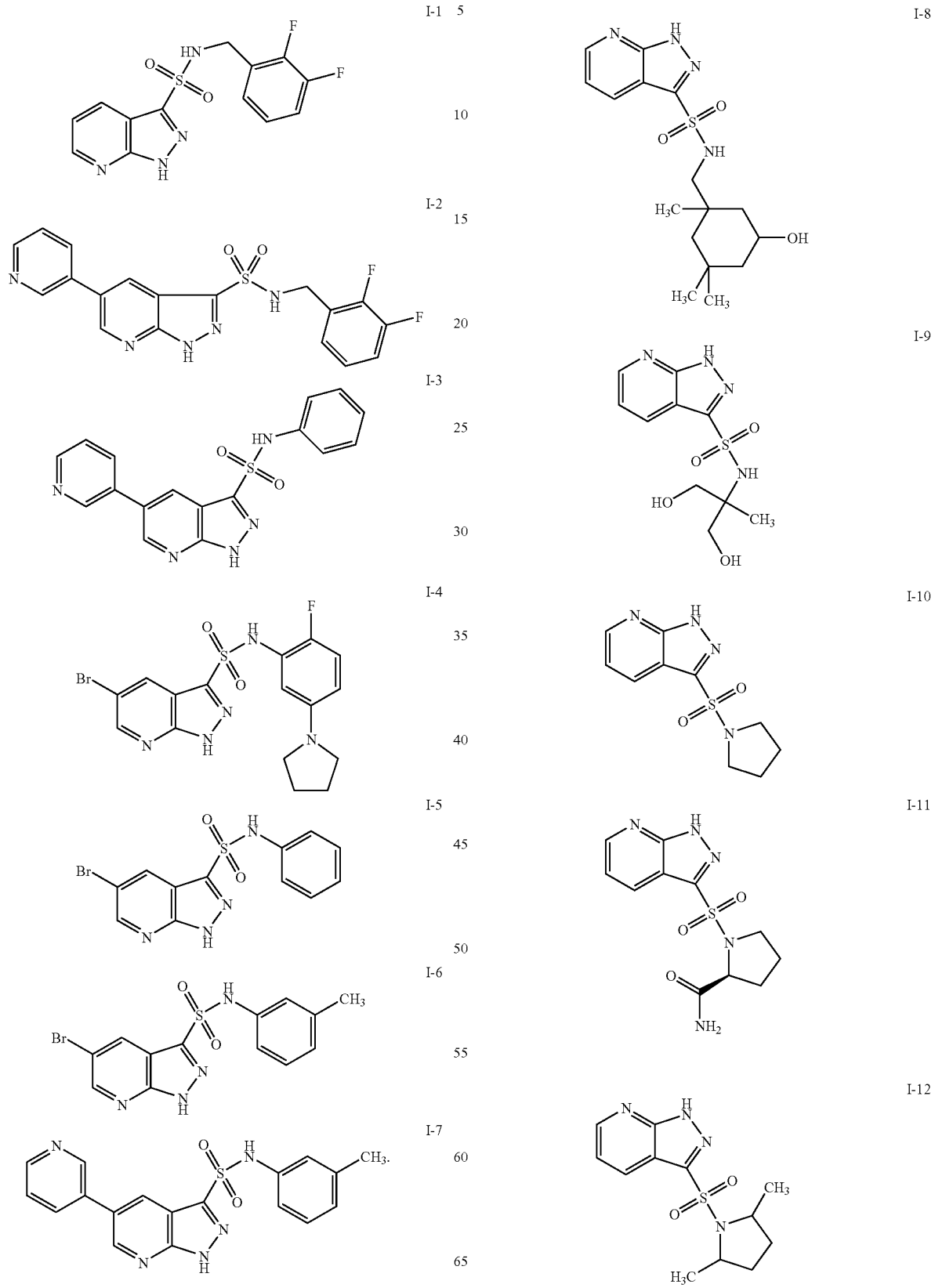

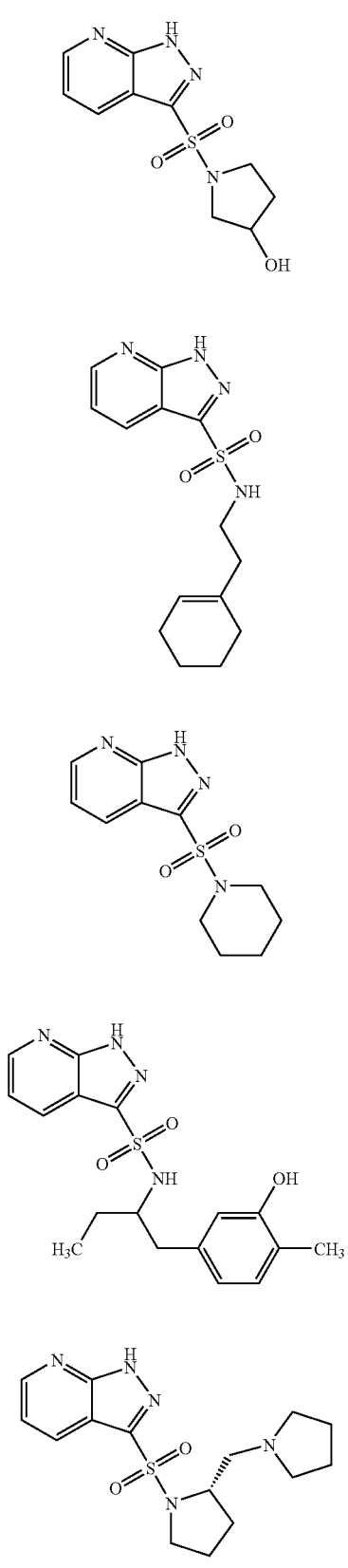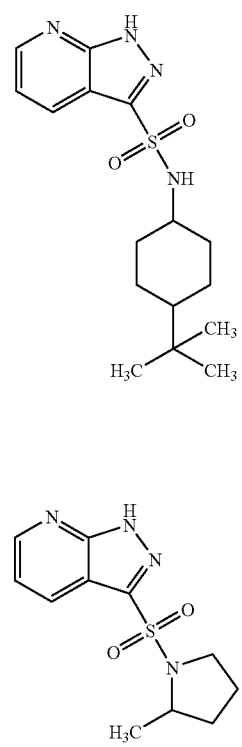

| | |
|---|---|
| I-22 | I-26 |
| I-23 | I-27 |
| I-24 | I-28 |
| I-25 | I-29 |

-continued
I-30
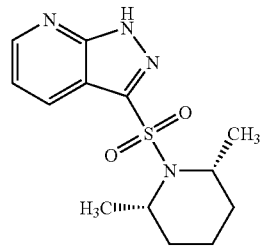
I-31
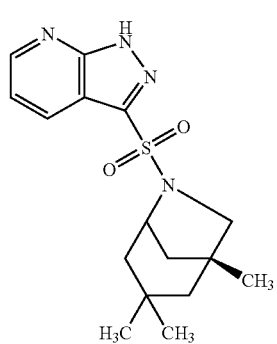
I-32
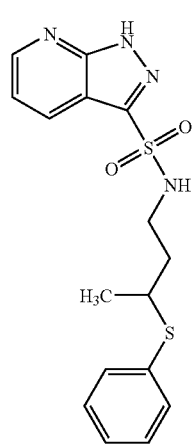
I-33
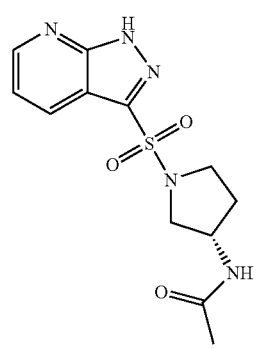
-continued
I-34
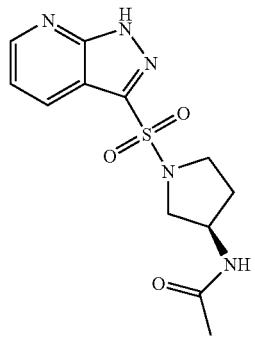
I-35
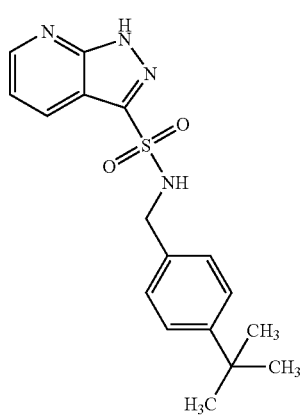
I-36
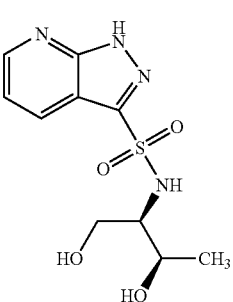
I-37
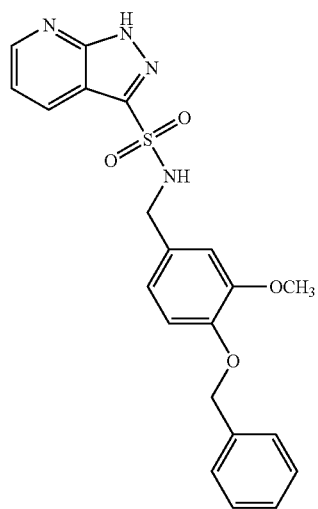

I-38
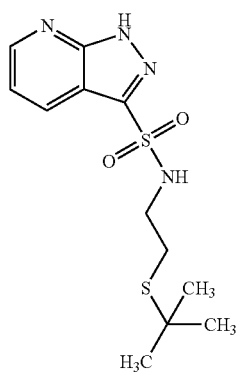
I-39
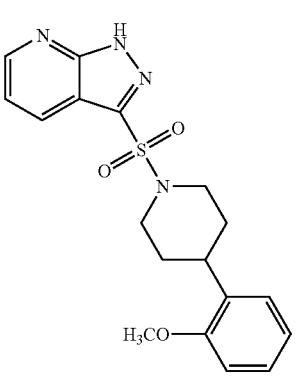
I-40
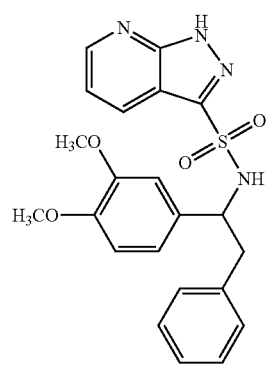
I-41
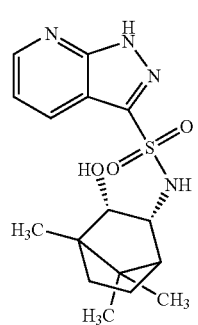
I-42
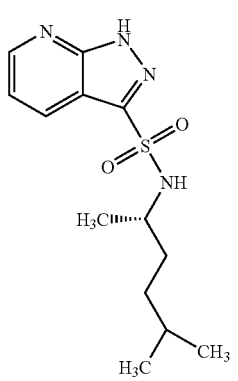
I-43
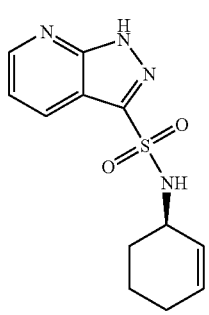
I-44
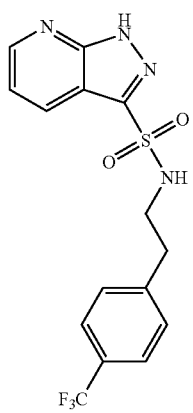
I-45
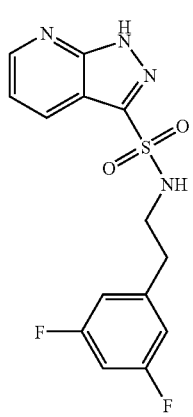

I-46 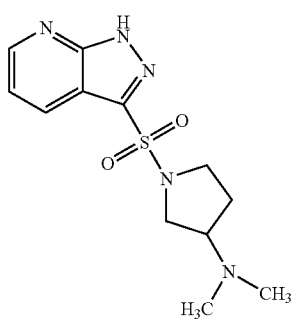
I-47 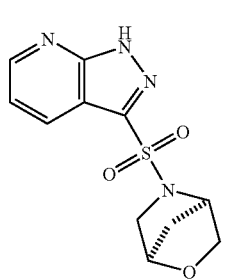
I-48 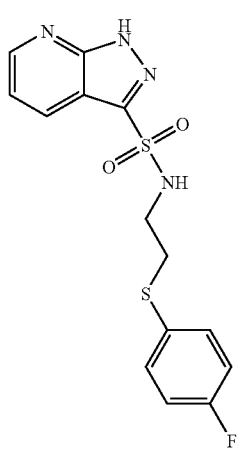
I-49 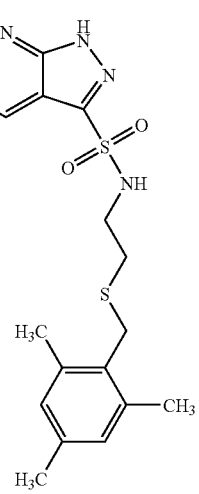
I-50 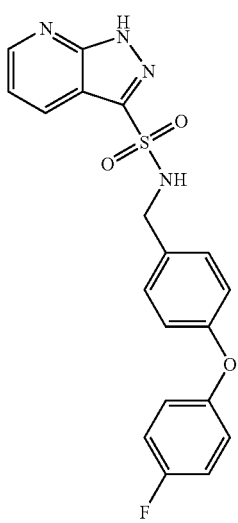
I-51 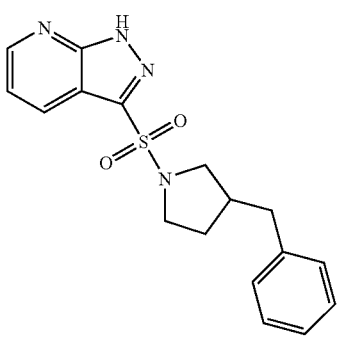
I-52 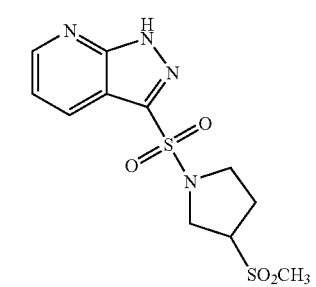
I-53 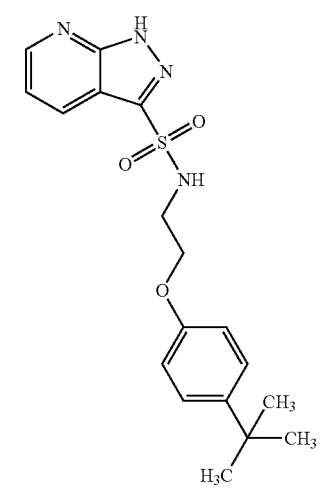

I-54
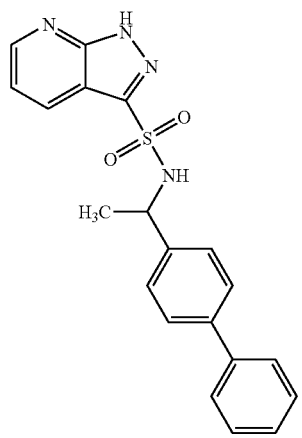
I-55
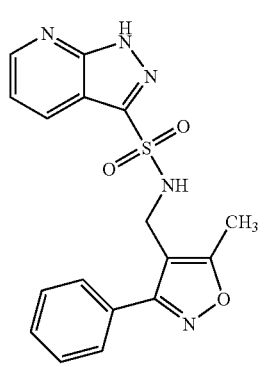
I-56
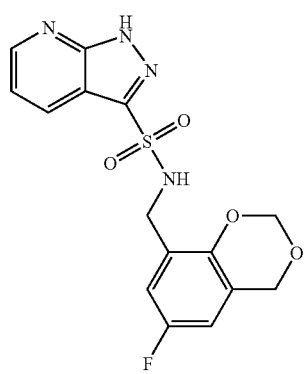
I-57
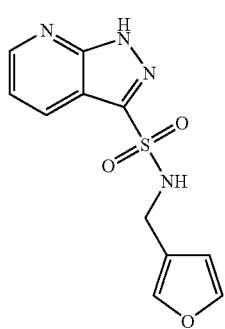
I-58
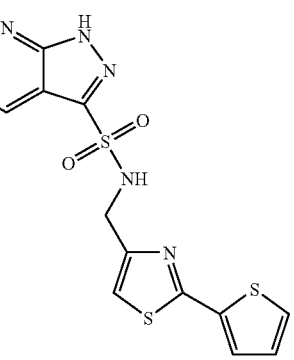
I-59
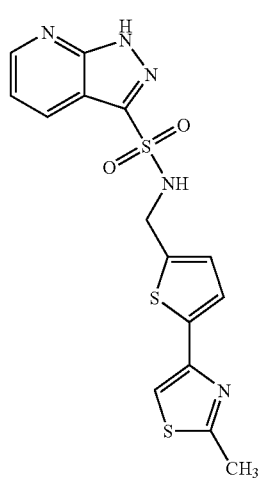
I-60
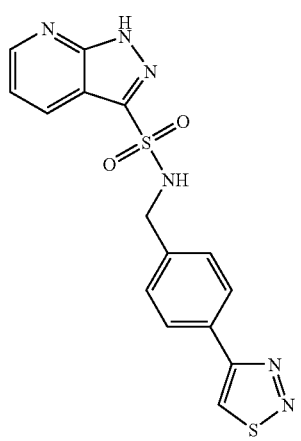
I-61
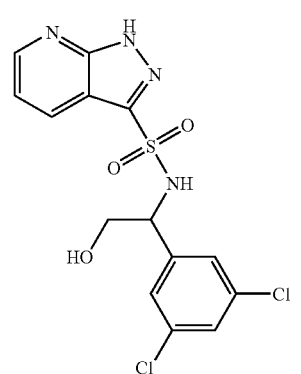

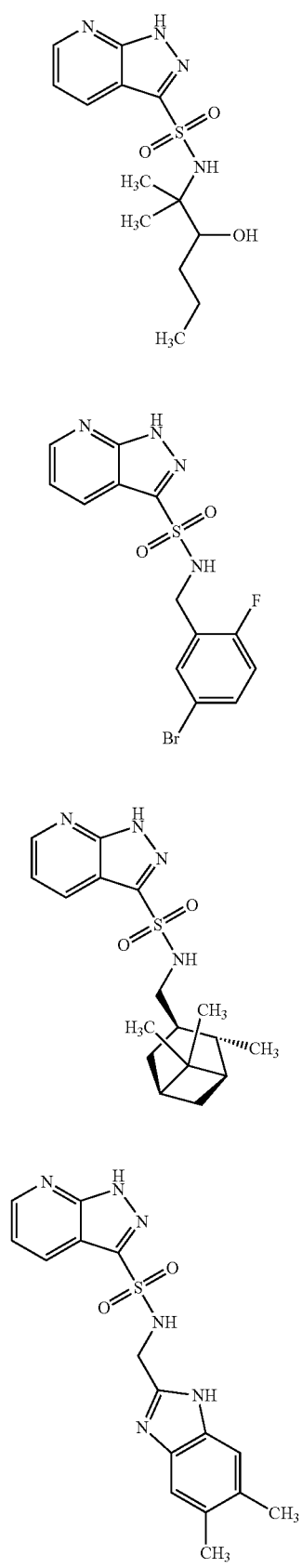
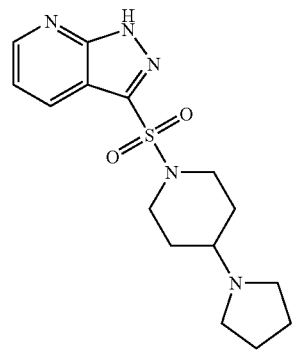

I-71 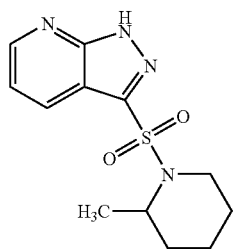
I-72 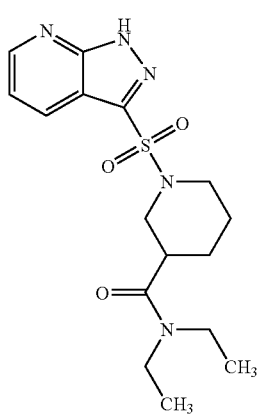
I-73 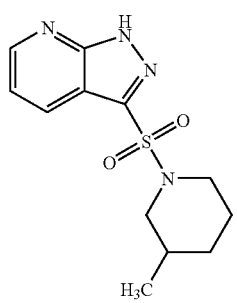
I-74 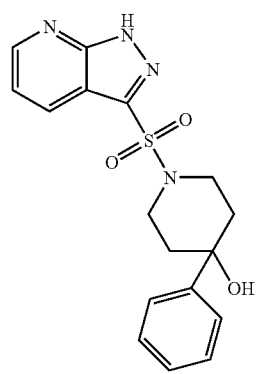
I-75 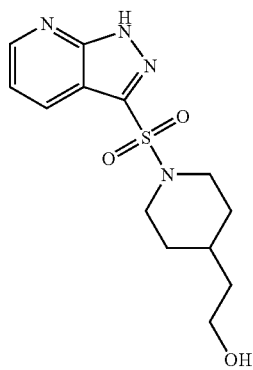
I-76 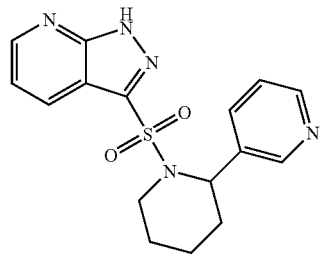
I-77 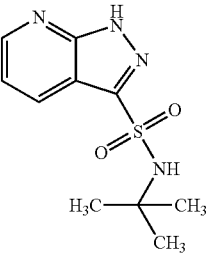
I-78 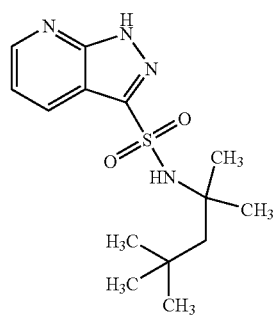
I-79 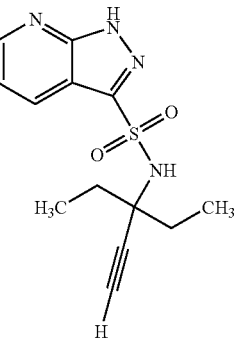

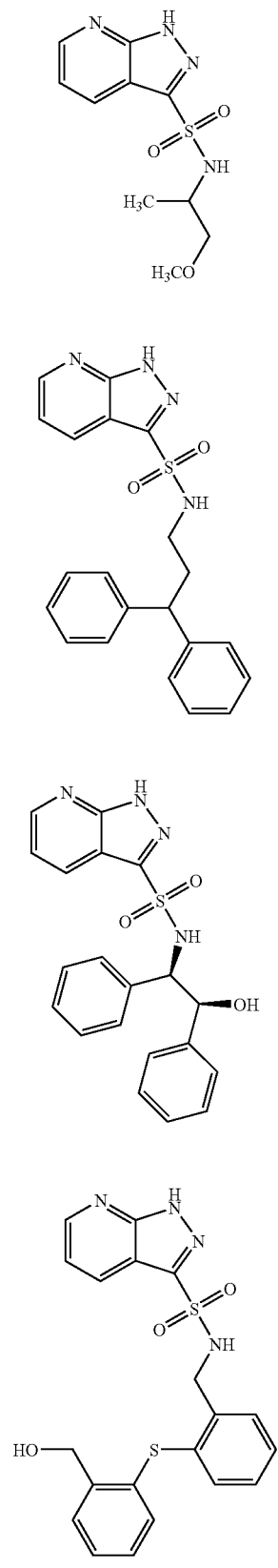
I-80
I-81
I-82
I-83
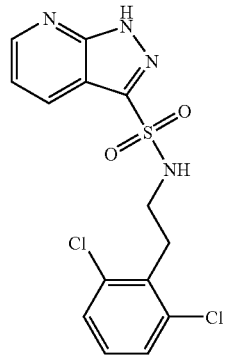
I-84
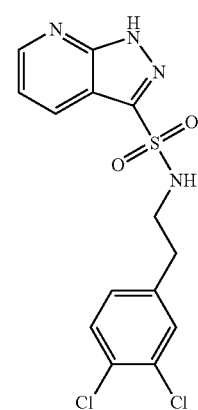
I-85
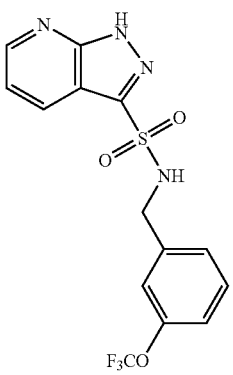
I-86
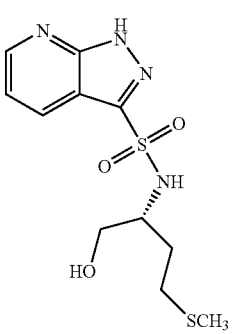
I-87

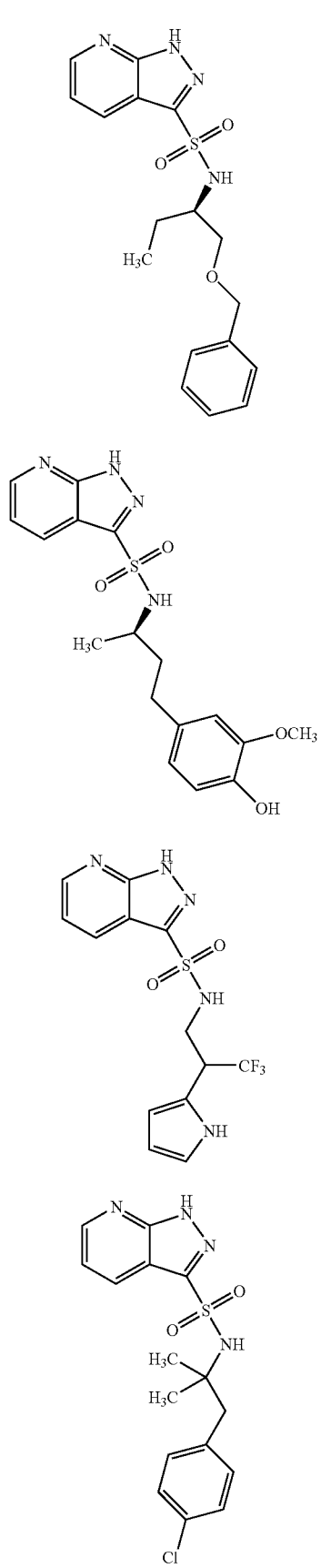
I-88
I-89
I-90
I-91
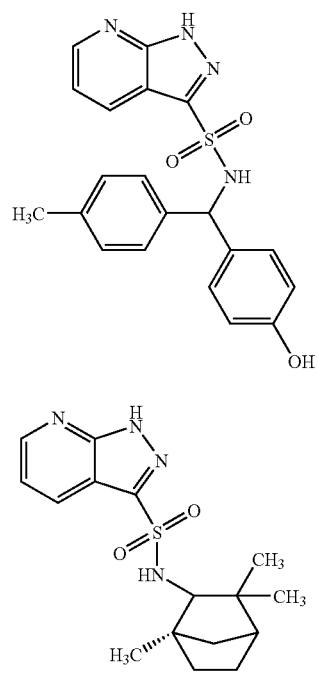
I-92
I-93
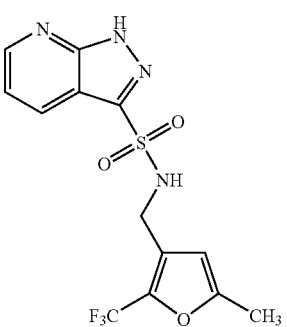
I-94
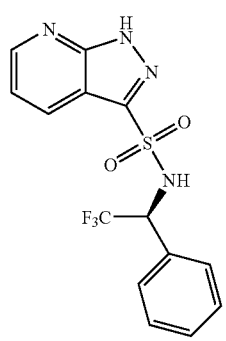
I-95
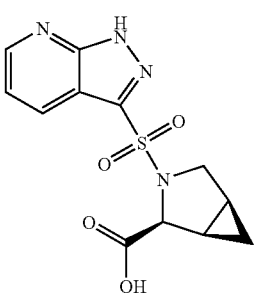
I-96

I-97 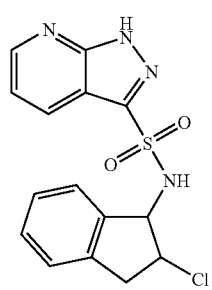
I-98 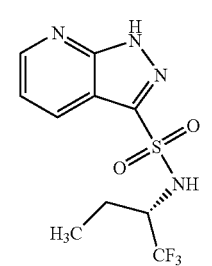
I-99 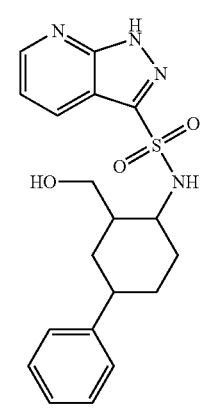
I-100 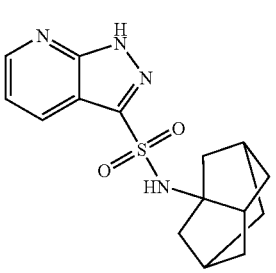
I-101 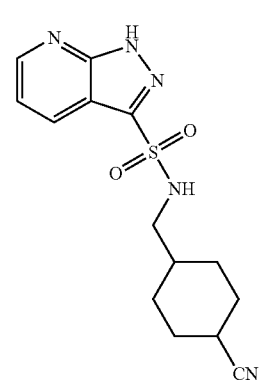
I-102 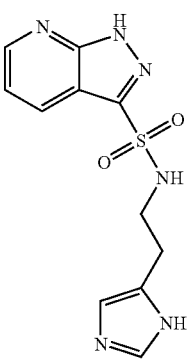
I-103 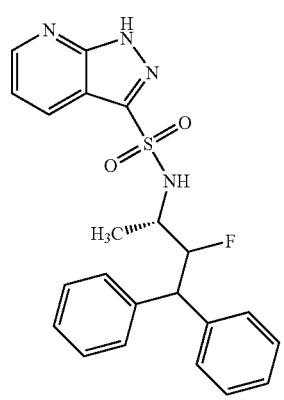
I-104 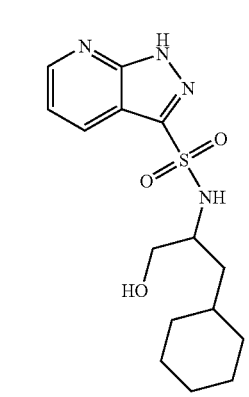
I-105 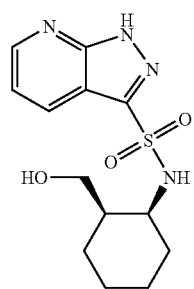

-continued

I-106

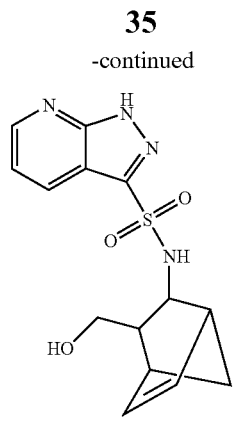

I-107

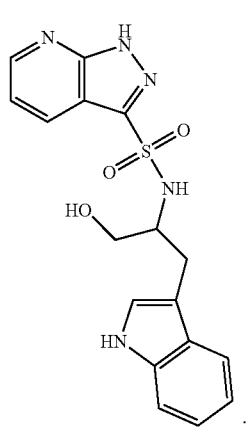

General Synthetic Methodology

The compounds of this invention may be prepared in general by methods such as those depicted in the general schemes below, and the preparative examples that follow. It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Starting materials shown are either commercially available or can be readily accessible from methods known to one skilled in the art. Unless otherwise indicated, all variables in the following schemes are as defined herein.

Scheme I

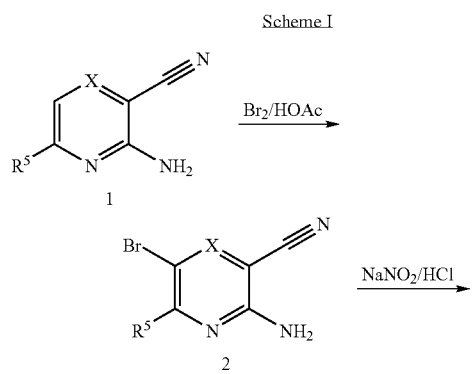

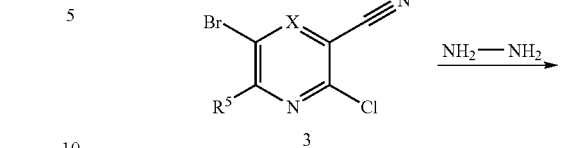

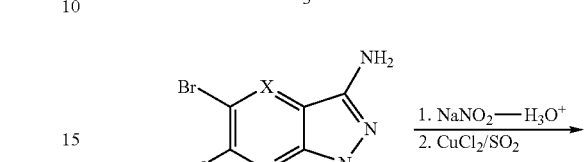

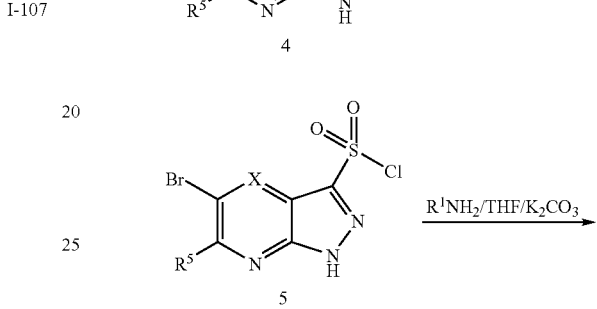

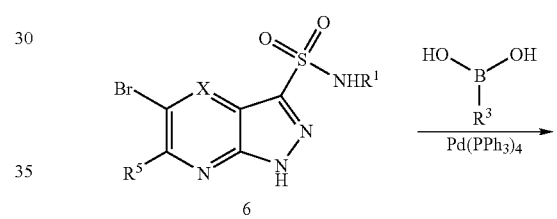

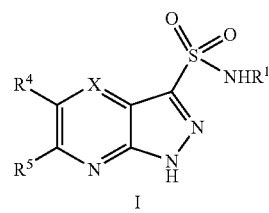

Scheme I above shows a general synthetic route that is used for preparing the compounds of formula I wherein X, $R^1$, $R^4$, and $R^5$ are as described herein. As would be recognized by one skilled in the art, the specific conditions depicted can be replaced with other known conditions in the art. The compound of formula 1 is brominated under suitable bromination conditions known to one skilled in the art to form a compound of formula 2. The compound of formula 2 is then chlorinated to form a compound of formula 3, which, in the presence of hydrazine, is cyclized to form a compound of formula 4. The compound of formula 4 is then first mixed in the presence of $NaNO_2$—$H_3O+$, and then in the presence of $CuCl_2/SO_2$, to form a sulfonyl chloride, which, upon mixing with a desired amine ($R^1$—$NH_2$), forms a compound of formula 6. The compound of formula 6 is mixed with a desired boronic acid ($R^3$—$B(OH)_2$) in the presence of a suitable catalyst (such as a palladium catalyst) to form the compound of formula I.

Scheme II

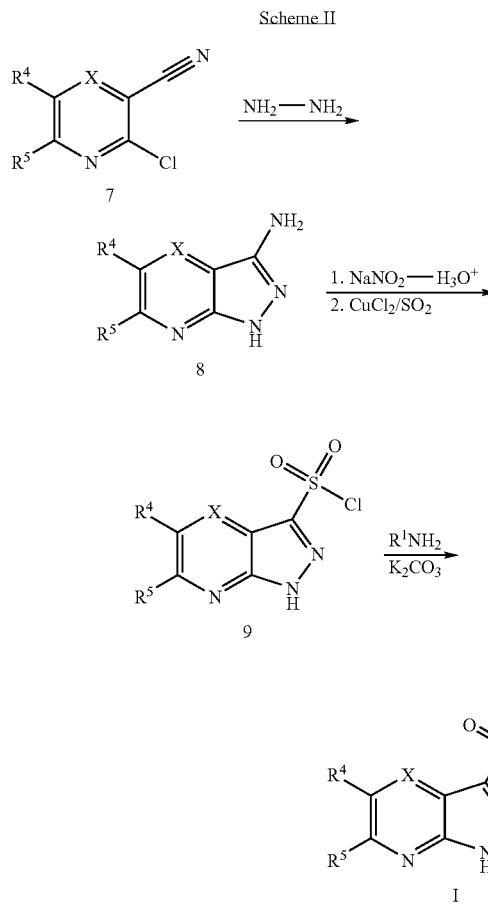

Scheme II shows another method for preparing the compounds I wherein X, $R^1$, $R^4$, and $R^5$ are as described herein. As would be recognized by one skilled in the art, the specific conditions depicted can be replaced with other known conditions in the art. The compound of formula 7 is heated in the presence of hydrazine, cyclizing to form a compound of formula 8. The compound of formula 8 is then first mixed in the presence of $NaNO_2$—$H_3O+$, and then in the presence of $CuCl_2/SO_2$, to form a sulfonyl chloride, which, upon mixing with a desired amine ($R^1$—$NH_2$), forms a compound of formula I.

One embodiment of this invention provides a process for preparing a compound of formula I:

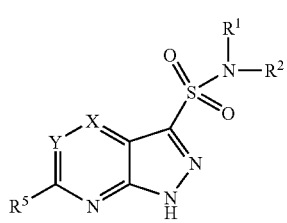

wherein Y is $CR^4$ and $R^1$, $R^2$, X, and $R^5$ are as defined herein, comprising reacting a compound of formula 6

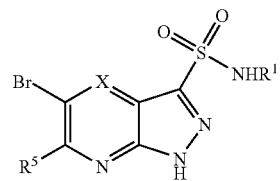

with $R^4$—BA, wherein BA is a suitable boronic acid or ester, under suitable Pd coupling conditions to form the compound of formula I.

Another embodiment further comprising the step of
a) reacting the compound of formula 4 with $NaNO_2$—$H_3O+$, and then with $CuCl_2/SO_2$ to form the desired sulfonyl chloride (formula 5)
b) reacting the compound of formula 5 with $R1$-$NH_2$ to form the compound of formula 6.

Another embodiment further comprising cyclizing the compound of formula 3;

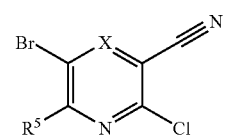

in the presence of hydrazine to form a compound of formula 4.

One embodiment provides a process for preparing a compound of formula I':

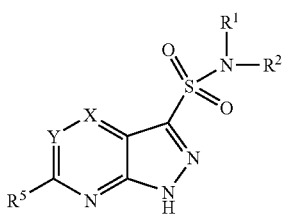

wherein Y is N and $R^1$, $R^2$, X, and $R^5$ are as defined herein, comprising the step of
a) reacting the compound of formula 4'

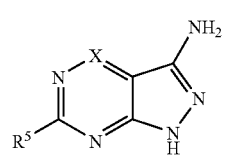

with $NaNO_2$—$H_3O+$, and then with $CuCl_2/SO_2$ to form the desired sulfonyl chloride (formula 5')

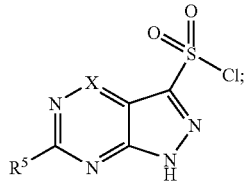

b) reacting the compound of formula 5' with R¹—NH₂ to form the compound of formula I'.

Another embodiment further comprising cyclizing the compound of formula 3';

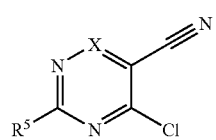

in the presence of hydrazine to form a compound of formula 4'.

Another embodiment of this invention provides a process for preparing a compound of formula I:

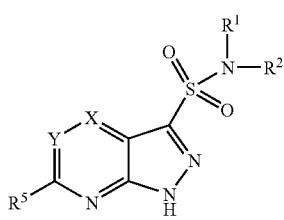

wherein Y is CR⁴, R² is H, and R¹, X, and R⁵ are as defined in any one of the claims, comprising:

a) cyclizing a compound of formula 7

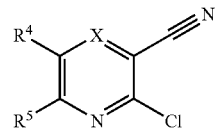

in the presence of hydrazine to form a compound of formula 8;

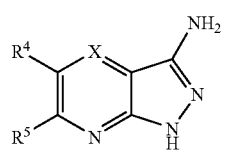

b) reacting the compound of formula 8 with NaNO₂—H₃O+, and then with CuCl₂/SO₂ to form the desired sulfonyl chloride of formula 9;

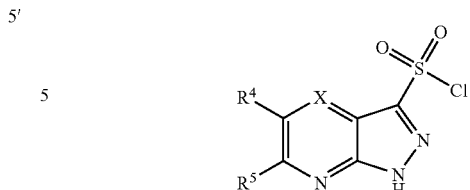

and c) reacting a compound of formula 9 with R¹—NH₂ to form a compound of Formula I wherein R¹, R⁴, and R⁵ are as defined according to any one of the claims.

Another embodiment of this invention provides a process for preparing a compound of formula I:

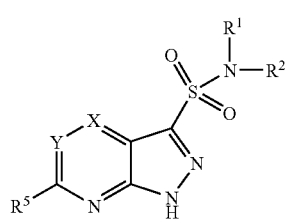

wherein Y is CR⁴, R² is H, and R¹, X, and R⁵ are as defined herein, comprising reacting a compound of formula 9 with R¹—NH₂.

Another embodiment further comprises the step of reacting the compound of formula 8 with NaNO₂—H₃O+, and then with CuCl₂/SO₂ to form the desired sulfonyl chloride of formula 9.

Another embodiment further comprises the step of cyclizing the compound of formula 7 in the presence of hydrazine to form a compound of formula 8.

Accordingly, this invention also provides a process for preparing a compound of this invention.

As discussed above, the present invention provides compounds that are inhibitors of protein kinases, and thus the present compounds are useful for the treatment of diseases, disorders, and conditions including, but not limited to an autoimmune, inflammatory, proliferative, or hyperproliferative disease or an immunologically-mediated disease.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a PLK1 protein kinases kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference.

Pharmaceutically acceptable salts of the compounds of this invention include those derived from pharmaceutically acceptable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other examples of pharmaceutically acceptable salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate (tosylate), undecanoate, valerate salts, and the like.

Base addition salts can be prepared by 1) reacting the purified compound in its acid form with a suitable organic or inorganic base and 2) isolating the salt thus formed. Base addition salts include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Other acids and bases, while not in themselves pharmaceutically acceptable, may be employed in the preparation of salts useful as intermediates in obtaining the compounds of the invention and their pharmaceutically acceptable acid or base addition salts.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

As described generally above, the compounds of the invention are useful as inhibitors of protein kinases. In one embodiment, the compounds and compositions of the invention are inhibitors PLK1 kinase, and thus, the compounds and compositions are particularly useful for treating or lessening the severity of a disease, condition, or disorder where activation of PLK1 kinase is implicated in the disease, condition, or disorder. When activation of PLK1 is implicated in a particular disease, condition, or disorder, the disease, condition, or disorder may also be referred to as a "PLK1-mediated disease" or disease symptom. Accordingly, in another aspect, the present invention provides a method for treating or lessening the severity of a disease, condition, or disorder where activation of PLK1 is implicated in the disease state.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is a PLK1-mediated condition.

The term "protein kinase-mediated condition", as used herein means any disease or other deleterious condition in which a protein kinase is known to play a role. Such conditions include, without limitation, autoimmune diseases, inflammatory diseases, neurological and neurodegenerative diseases, cancer, cardiovascular diseases, allergy and asthma.

The term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

The term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, non-small cell, adenocarcinoma, alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer.

The term "PLK1-mediated condition", as used herein means any disease or other deleterious condition in which PLK1 is known to play a role. Such conditions include, without limitation, a proliferative disorder, such as cancer, a neurodegenerative disorder, an autoimmune disorder, and inflammatory disorder, and an immunologically-mediated disorder.

In some embodiments, the compounds of this invention are useful for treating cancer, such as colorectal, thyroid, breast, and non-small cell lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

In other embodiments, the compounds of this invention are useful for treating immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas.

In some embodiments, the compounds of this invention are useful for treating allergic or type I hypersensitivity reactions, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), schizophrenia, cardiomyocyte hypertrophy, reperfusion/ischemia, stroke, baldness, transplant rejection, graft versus host disease, rheumatoid arthritis, amyotrophic lateral sclerosis, and multiple sclerosis, and solid and hematologic malignancies such as leukemias and lymphomas. In a further embodiment, said disease or disorder is asthma. In another embodiment, said disease or disorder is transplant rejection.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

In yet another aspect, a method for the treatment or lessening the severity of a protein kinase-mediated disease is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for a PLK1-mediated disease. The compounds and compositions, according to the method of the present invention, may be administered using any amount and any route of administration effective for treating or lessening the severity of a protein kinase-mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, said protein-kinase is PLK.

In another embodiment, the invention comprises a method of treating or lessening the severity of a disease or condition selected from: immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas comprising administering to said patient a compound or composition of the invention.

In another embodiment, the invention provides a method of treating or lessening the severity of a disease or condition selected from a proliferative disorder, a cardiac disorder, a neurodegenerative disorder, an autoimmune disorder, a condition associated with organ transplant, an inflammatory disorder, an immune disorder or an immunologically mediated disorder, comprising administering to said patient a compound or composition of the invention.

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

In one embodiment, the disease or disorder is allergic or type I hypersensitivity reactions, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), schizophrenia, cardiomyocyte hypertrophy, reperfusion/ischemia, stroke, baldness, transplant rejection, graft versus host disease, rheumatoid arthritis, amyotrophic lateral sclerosis, and multiple sclerosis, and solid and hematologic malignancies such as leukemias and lymphomas. In a further embodiment, said disease or disorder is asthma. In another embodiment, said disease or disorder is transplant rejection.

According to another embodiment, the invention provides methods for treating or preventing a PLK1-mediated condition comprising the step of administering to a patient one of the above-described pharmaceutical compositions.

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease or disorder described above.

According to another embodiment, the invention provides methods for treating or preventing cancer comprising the step of administering to a patient one of the above-described pharmaceutical compositions.

Another aspect of the invention relates to inhibiting PLK1 activity in a patient, which method comprises administering to the patient a compound of formula I or a composition comprising said compound.

Another aspect of the invention relates to a method which comprises the step of disrupting mitosis of the cancer cells by inhibiting PLK1 with a compound of formula I or a composition comprising said compound.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Administering with Another Agent

Depending upon the particular PLK1-mediated conditions to be treated or prevented, additional drugs, which are normally administered to treat or prevent that condition, may be administered together with the inhibitors of this invention. For example, chemotherapeutic agents or other anti-proliferative agents may be combined with the PLK1 inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the kinase inhibitor in a single composition.

Another aspect of the invention relates to inhibiting PLK1 activity in a biological sample or a patient, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of kinases in biological and pathological phenomena; the study of intracellular signal transduction pathways mediated by such kinases; and the comparative evaluation of new kinase inhibitors. Examples of such uses include, but are not limited to, biological assays such as enzyme assays and cell-based assays.

In order that this invention be more fully understood, the following examples are set forth. Compounds of this invention may be tested according to these examples. These examples are for the purpose of illustration only and are not to be construed as limiting the scope of the invention in any way.

EXAMPLES

Scheme I-a

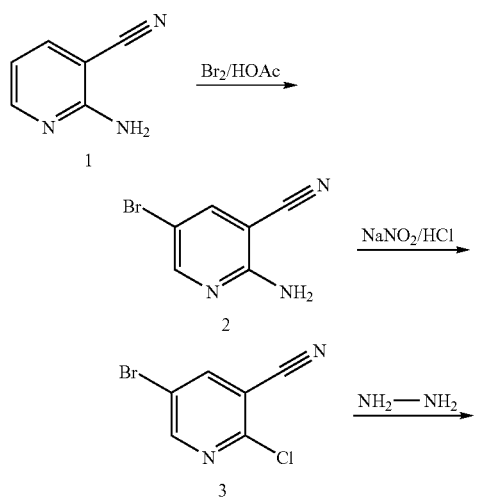

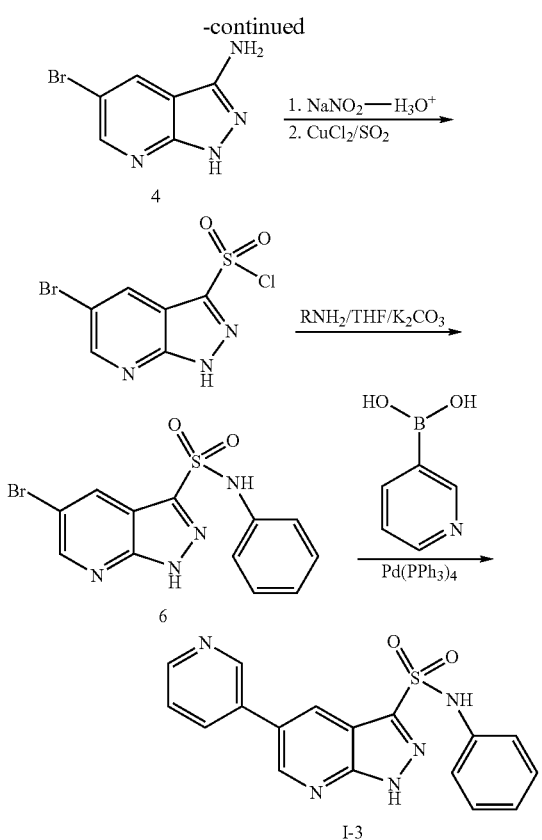

Example 1

2-amino-5-bromopyridine-3-carbonitrile (2)

2-aminopyridine-3-carbonitrile 1 (0.56 g, 4.6 mmol) was dissolved in 10 mL HOAC, to which one equivalent of $Na_2CO_3$ was added. Then, 1.1 equivalent of $Br_2$ was added dropwise and reaction mixture was stirred at room temperature for 30 minutes. Orange precipitation was formed and filtered off to obtain the desired compound 2 in quantitative yield. The compound was carried on without further purification.

Example 2

5-bromo-2-chloropyridine-3-carbonitrile (3)

Compound 2 was dissolved in conc. HCl at 0° C., to which 1.1 equivalent of $NaNO_2$ in $H_2O$ was added dropwise. Precipitation was formed. The white solid was filtered off, which gave the title compound 3. Overall yield was 70%.

Example 3

5-bromo-1H-pyrazolo[3,4-b]pyridin-3-amine (4)

Compound 3 (307 mg, 1.4 mmol) was dissolved in EtOH (10 mL) in a microwave tube, to which 5 equivalent of $NH_2NH_2$ was added, and the reaction mixture was put on Microwave irradiation for 10 min at 170° C. Evaporated the solvent to obtain the title compound 4 in quantative yield.

Example 4

5-bromo-1H-pyrazolo[3,4-b]pyridine-3-sulfonyl chloride (5)

Compound 4 (0.45 mmol) was dissolved in a mixture of 10 N HCl (0.1 mL), acetic acid (1 mL) and formic acid (0.1 mL) at 0° C., NaNO₂ (1.2 equiv) in H₂O (0.06 mL) was added, while maintaining the temperature at 0° C., the diazo solution was stirred for an additional 10 minutes and then poured portion wise into a freshly prepared mixture of CuCl₂ dihydrate (18 mg) and acetic acid (0.4 mL) in which SO₂ (126 mg) had been dissolved at room temperature. The reaction mixture was stirred at room temperature for 15 minutes and then evaporated to dryness. The residue was extracted with ether, dried over sodium sulfate, and the solvent was evaporated to obtain the title compound 5.

Example 6

Phenyl 5-bromo-1H-pyrazolo[3,4-b]pyridine-3-sulfonylamide (6)

Compound 5 was dissolved in dry THF, 1 equivalent of K₂CO₃ was added, followed by 1.2 equivalent of aniline. The reaction mixture was stirred at 80° C. overnight to give compound 6. The solvent was evaporated and the reaction was carried on to the next step without further purification.

Example 7

Phenyl 5-(3-pyridyl)-1H-pyrazolo[3,4-b]pyridine-3-sulfonylamide (I-3)

Reaction mixture of compound 6 (50 mg, 0.14 mmol) was in microwave tube, 1.5 equivalent of pyridin-3-yl-3-boronic acid, 3 equivalent of K₂CO₃ was added, followed by 2 mL of dioxane and 1 mL of H₂O, to this reaction mixture, 10% of Pd(PPh₃)₄ was added and reaction mixture was put in Microwave irradiation at 150° C. for 10 min. The organic lay was separated and dried down The reaction mixture was redissolved in EtOAc, the organic was washed with H₂O and brine and dried over Na₂SO₄. The solvent was evaporated from the reaction mixture, and the mixture was subjected to prep HPLC for separation to obtain the title compound I-3. MS+1=352.3.

Scheme II-a

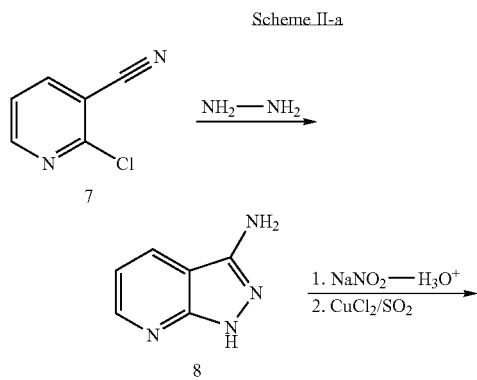

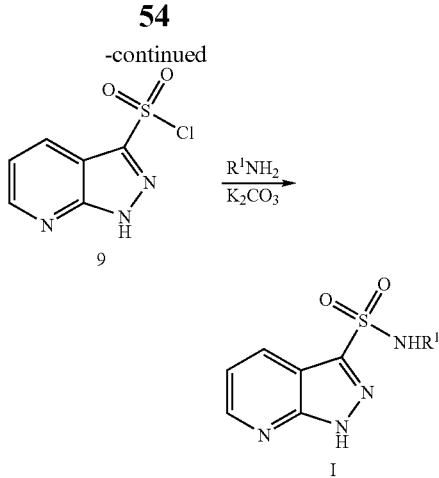

Example 8

Compound 7 (1.4 mmol) was dissolved in EtOH (10 mL) in a microwave tube, to which 5 equivalent of NH₂NH₂ was added, and the reaction mixture was heated by microwave irradiation for 10 min at 170° C. Evaporated the solvent to obtain the compound 8 in quantitative yield.

Compound 8 (0.45 mmol) was dissolved in a mixture of 10 N HCl (0.1 mL), acetic acid (1 mL) and formic acid (0.1 mL) at 0° C., NaNO₂ (1.2 equiv) in H₂O (0.06 mL) was added, while maintaining the temperature at 0° C., the diazo solution was stirred for an additional 10 minutes and then poured portion-wise into a freshly prepared mixture of CuCl₂ dihydrate (18 mg) and acetic acid (0.4 mL) in which SO₂ (126 mg) had been dissolved at room temperature. The reaction mixture was stirred at room temperature for 15 minutes and then evaporated to dryness. The residue was extracted with ether, dried over sodium sulfate, and the solvent was evaporated to obtain the title compound 9.

Compound 9 was dissolved in dry THF. 1 equivalent of K₂CO₃ was then added to the solution, followed by 1.2 equivalents of amine. The reaction mixture was stirred at 80° C. overnight. The solvent was then evaporated to give compounds of formula I (in Scheme II-a) wherein R¹ is as defined herein.

LCMS Method A

Mass spec. samples were analyzed on a MicroMass ZQ, ZMD or Quattro II mass spectrometer operated in single MS mode with electrospray ionization. Samples were introduced into the mass spectrometer using flow injection (FIA) or chromatography. Mobile phase for all mass spec. analysis consist of acetonitrile-water mixtures with either 0.2% formic acid or 0.1% TFA as a modifier. Column gradient conditions are 10%-90% acetonitrile over 3 mins gradient time and 5 mins run time on a Waters YMC Pro-C18 4.6×50 mm column. Flow rate is 1.5 ml/min.

LCMS Method B

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions are 10%-100% acetonitrile-methanol over 3.5 mins gradient time and 5 mins run time on an ACE C8 3.0×75 mm column. Flow rate is 1.2 ml/min.

Compounds I-1 to I-3 were analyzed according to Method A. Compounds I-4 to I-7 were analyzed according to Method B.
Compounds I-2 to I-7 were made according to Scheme I-a shown above. Compound I-1 was made according to Scheme II-a shown above.
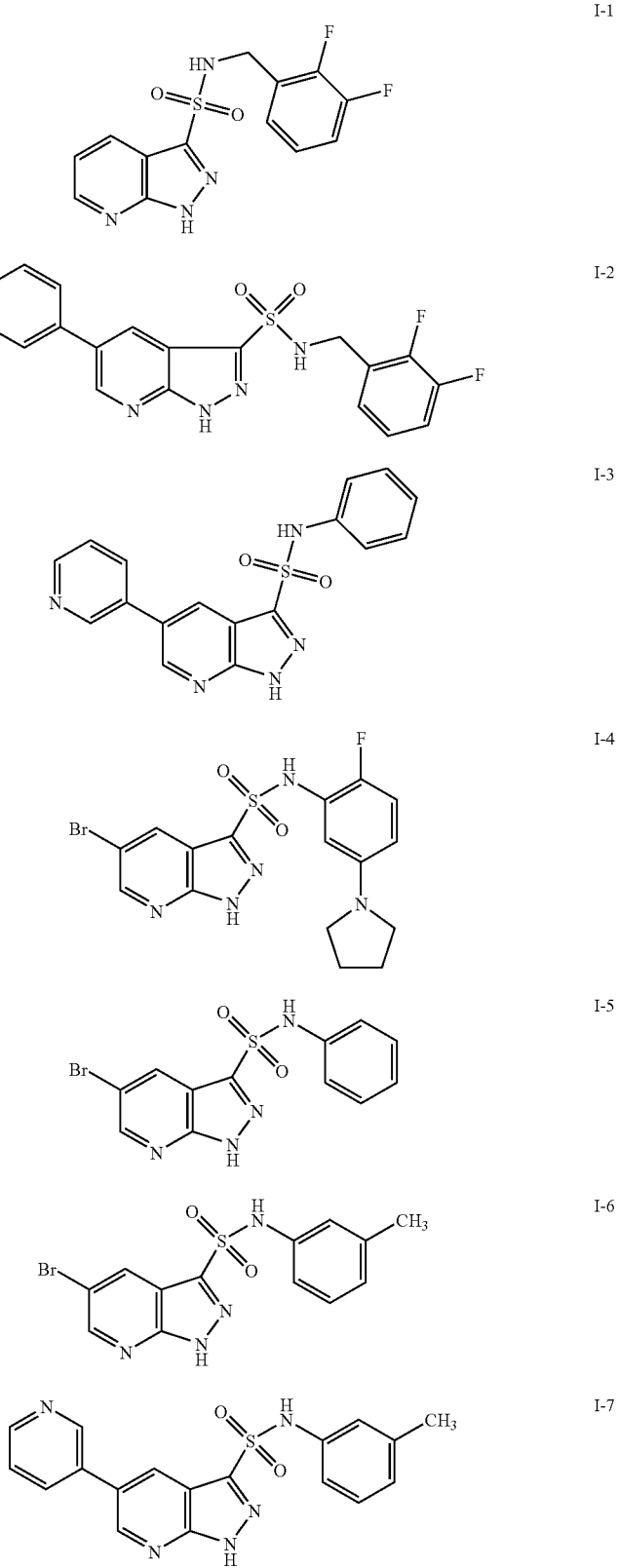

-continued

| Compound Number | M + 1 (obs) | HNMR | LCMS Rt (min) | QC Rt (min) |
|---|---|---|---|---|
| I-1 | 324.70 | (MeOD) 8.6d (1H), 8.4d (1H), 7.35q (2H), 7.0m (2H), 6.9m (1H), 4.4s (2H) | 2.76 | — |
| I-2 | 402.00 | (MeOD) 9.1bs (1H), 9.0s (1H), 8.8bs (1H), 8.6s (1H), 8.6d (1H), 8.0bs (1H), 7.0m (3H), 4.4s (2H) | 1.90 | — |
| I-3 | 351.80 | (DMSO) 14.7s (1H), 10.7s (1H), 9.0d (2H), 8.7d (1H), 8.6s (1H), 8.3d (1H), 7.7m (1H). 7.2m (2H), 7.15m (2H), 7.05m (1H) | 1.84 | — |
| I-4 | 440.26 | (DMSO) 1.92 (4H, brs), 3.06 (4H, brs), 6.25 (1H, m), 6.37 (1H, m). 6.89 (1H, t), 8.27 (1H, s), 8.74 (1H, s), 10.39 (NH) | 3.48 | 9.424 |
| I-5 | 353.22 | (DMSO) 7.08 (1H, t), 7.20 (2H, m), 7.30 (2H, m), 8.44 (1H, s), 8.78 (1H, s), 10.75 (NH) | 3.16 | 8.498 |
| I-6 | 367.15 | (DMSO) 2.20 (3H, s), 6.94 (2H, m), 7.02 (1H, s), 7.15 (1H, m), 8.40 (1H, s), 8.75 (1H, s), 10.65 (NH) | 3.49 | 9.000 |
| I-7 | 366.29 | (DMSO) 2.19 (3H, s), 6.81 (1H, m), 6.95 (1H, m), 7.05 (1H, s), 7.10 (1H, t), 7.59 (1H, m), 8.17 (1H, m), 8.46 (1H, s), 8.68 (1H, m), 8.96 (1H, s), 9.02 (1H, s), 10.68 (NH) | 3.16 | 7.957 |

Example 9

PLK1 Assay

The compounds of the present invention may be evaluated as inhibitors of human PLK kinase using the following assays.

Plk1 Inhibition Assay:

Compounds can be screened for their ability to inhibit Plk1 using a radioactive-phosphate incorporation assay. Assays are carried out in a mixture of 25 mM HEPES (pH 7.5), 10 mM MgCl2, and 1 mM DTT. Final substrate concentrations are 50 μM [γ-33P]ATP (136 mCi 33P ATP/mmol ATP, Amersham Pharmacia Biotech/Sigma Chemicals) and 10 μM peptide (SAM68 protein Δ332-443). Assays are carried out at 25° C. in the presence of 15 nM Plk1 (A20-K338). An assay stock buffer solution is prepared containing all of the reagents listed above, with the exception of ATP and the test compound of interest. 30 μL of the stock solution is placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate is pre-incubated for 10 minutes at 25° C. and the reaction initiated by addition of 8 μL [γ-33P]ATP (final concentration 50 μM).

The reaction is stopped after 60 minutes by the addition of 100 μl 0:14M phosphoric acid. A multiscreen phosphocellulose filter 96-well plate (Millipore, Cat no. MAPHN0B50) is pretreated with 100 μL 0.2M phosphoric acid prior to the addition of 125 μL of the stopped assay mixture. The plate is washed with 4×200 μL 0.2M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

Plk2 Inhibition Assay:

Compounds can be screened for their ability to inhibit Plk2 using a radioactive-phosphate incorporation assay. Assays are carried out in a mixture of 25 mM HEPES (pH 7.5), 10 mM MgCl2, 0.1% BSA, and 2 mM DTT. Final substrate concentrations are 200 μM [-33P]ATP (57 mCi 33P ATP/mmol ATP, Amersham Pharmacia Biotech/Sigma Chemicals) and 300 μM peptide (KKKISDELMDATFADQEAK (SEQ ID NO: 1)). Assays are carried out at 25° C. in the presence of 25 nM Plk2. An assay stock buffer solution is prepared containing all of the reagents listed above, with the exception of ATP and the test compound of interest. 30 μL of the stock solution is placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate is pre-incubated for 10 minutes at 25° C. and the reaction initiated by addition of 8 μL [γ-33P] ATP (final concentration 200 μM).

The reaction is stopped after 90 minutes by the addition of 100 μL 0.14M phosphoric acid. A multiscreen phosphocellulose filter 96-well plate (Millipore, Cat no. MAPHN0B50) is pretreated with 100 μL 0.2M phosphoric acid prior to the addition of 125 μL of the stopped assay mixture. The plate is washed with 4×200 μL 0.2M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

Plk3 Inhibition Assay:

Compounds can be screened for their ability to inhibit Plk3 using a radioactive-phosphate incorporation assay. Assays are carried out in a mixture of 25 mM HEPES (pH 7.5), 10 mM MgCl2, and 1 mM DTT. Final substrate concentrations are 75 μM [γ-33P]ATP (60 mCi 33P ATP/mmol ATP, Amersham Pharmacia Biotech/Sigma Chemicals) and 10 μM peptide (SAM68 protein Δ332-443). Assays are carried out at 25° C. in the presence of 5 nM Plk3 (S38-A340). An assay stock buffer solution is prepared containing all of the reagents listed above, with the exception of ATP and the test compound of interest. 30 μL of the stock solution is placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate is pre-incubated for 10 minutes at 25° C. and the reaction initiated by addition of 8 μL [γ-33P]ATP (final concentration 75 μM).

The reaction is stopped after 60 minutes by the addition of 100 μL 0.14M phosphoric acid. A multiscreen phosphocellulose filter 96-well plate (Millipore, Cat no. MAPHN0B50) is pretreated with 100 μL 0.2M phosphoric acid prior to the addition of 125 μL of the stopped assay mixture. The plate is washed with 4×200 μL 0.2M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif. USA).

Plk4 Inhibition Assay:

Compounds can be screened for their ability to inhibit Plk4 using a radioactive-phosphate incorporation assay. Assays are carried out in a mixture of 8 mM MOPS (pH 7.5), 10 mM MgCl2, 0.1% BSA and 2 mM DTT. Final substrate concentrations are 15 μM [γ-33P]ATP (227 mCi 33P ATP/mmol ATP, Amersham Pharmacia Biotech/Sigma Chemicals) and 300 μM peptide (KKKMDATFADQ (SEQ ID NO: 2)). Assays are carried out at 25° C. in the presence of 25 nM Plk4. An assay stock buffer solution is prepared containing all of the reagents listed above, with the exception of ATP and the test compound of interest. 30 μL of the stock solution is placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate is pre-incubated for 10 minutes at 25° C. and the reaction initiated by addition of 8 μL [γ-33P]ATP (final concentration 15 μM).

The reaction is stopped after 180 minutes by the addition of 100 μL 0.14M phosphoric acid. A multiscreen phosphocellulose filter 96-well plate (Millipore, Cat no. MAPHN0B50) is pretreated with 100 μL 0.2M phosphoric acid prior to the addition of 125 μL of the stopped assay mixture. The plate is washed with 4×200 μL 0.2M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

Example 10

JAK3 Inhibition Assay

Compounds can be screened for their ability to inhibit JAK using the assay shown below. Reactions are carried out in a kinase buffer containing 100 mM HEPES (pH 7.4), 1 mM DTT, 10 mM $MgCl_2$, 25 mM NaCl, and 0.01% BSA. Substrate concentrations in the assay are 5 μM ATP (200 uCi/μmole ATP) and 1 μM poly(Glu)$_4$Tyr (SEQ ID NO: 3). Reactions are carried out at 25° C. and 1 nM JAK3.

To each well of a 96 well polycarbonate plate is added 1.5 μl of a candidate JAK3 inhibitor along with 50 μl of kinase buffer containing 2 μM poly(Glu)$_4$Tyr (SEQ ID NO: 3) and 10 μM ATP. This is then mixed and 50 μl of kinase buffer containing 2 nM JAK3 enzyme is added to start the reaction. After 20 minutes at room temperature (25 C), the reaction is stopped with 50 μl of 20% trichloroacetic acid (TCA) that also contained 0.4 mM ATP. The entire contents of each well are then transferred to a 96 well glass fiber filter plate using a TomTek Cell Harvester. After washing, 60 μl of scintillation fluid is added and $^{33}P$ incorporation detected on a Perkin Elmer TopCount.

Example 11

JAK2 Inhibition Assay

The assays are as described above in Example 33 except that JAK-2 enzyme was used, the final poly(Glu)$_4$Tyr (SEQ ID NO: 3) concentration was 15 μM, and final ATP concentration was 12 μM.

Example 12

FLT-3 Inhibition Assay

Compounds can be screened for their ability to inhibit FLT-3 activity using a radiometric filter-binding assay. This assay monitors the 33P incorporation into a substrate poly (Glu, Tyr) 4:1 (pE4Y (SEQ ID NO: 3)). Reactions are carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay are 90 μM ATP and 0.5 mg/ml pE4Y (SEQ ID NO: 3) (both from Sigma Chemicals, St Louis, Mo.). The final concentration of a compound of the present invention is generally between 0.01 and 5 μM. Typically, a 12-point titration is conducted by preparing serial dilutions from 10 mM DMSO stock of test compound. Reactions are carried out at room temperature.

Two assay solutions are prepared. Solution 1 contains 100 mM HEPES (pH 7.5), 10 mM $MgCl_2$, 25 mM NaCl, 1 mg/ml pE4Y (SEQ ID NO: 3) and 180 mM ATP (containing 0.3 mCi of [-33$^P$]ATP for each reaction). Solution 2 contains 100 mM HEPES (pH 7.5), 10 mM $MgCl_2$, 25 mM NaCl, 2 mM DTT, 0.02% BSA and 3 nM FLT-3. The assay is run on a 96 well plate by mixing 50 μl each of Solution 1 and 2.5 ml of the compounds of the present invention. The reaction is initiated with Solution 2. After incubation for 20 minutes at room temperature, the reaction is stopped with 50 μl of 20% TCA containing 0.4 mM of ATP. All of the reaction volume is then transferred to a filter plate and washed with 5% TCA by a Harvester 9600 from TOMTEC (Hamden, Conn.). The amount of $^{33}P$ incorporation into pE4y (SEQ ID NO: 3) is analyzed by a Packard Top Count Microplate Scintillation Counter (Meriden, Conn.). The data is fitted using Prism software to get an IC50 or Ki.

Example 13

GSK-3 Inhibition Assay

Compounds can be screened for their ability to inhibit GSK-3 (AA 1-420) activity using a standard coupled enzyme system (Fox et al. (1998) *Protein Sci.* 7, 2249). Reactions are carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay are 20 μM ATP (Sigma Chemicals, St Louis, Mo.) and 300 μM peptide (HSSPHQS(PO$_3$H$_2$)EDEEE (SEQ ID NO: 4), American Peptide, Sunnyvale, Calif.). Reactions are carried out at 30° C. and 20 nM GSK-3. Final concentrations of the components of the coupled enzyme system are 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above with the exception of ATP and the test compound of interest. The assay stock buffer solution (175 µl) is incubated in a 96 well plate with 5 µl of the test compound of interest at final concentrations spanning 0.002 µM to 30 µM at 30° C. for 10 minutes. Typically, a 12-point titration is conducted by preparing serial dilutions (from 10 mM compound stocks) with DMSO of the test compounds in daughter plates. The reaction is initiated by the addition of 20 µl of ATP (final concentration 20 µM). Rates of reaction are obtained using a Molecular Devices Spectramax plate reader (Sunnyvale, Calif.) over 10 minutes at 30° C. The $K_i$ values are determined from the rate data as a function of inhibitor concentration.

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:
1. A compound selected from the following:
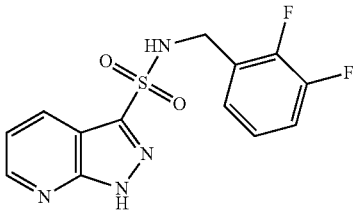
I-1
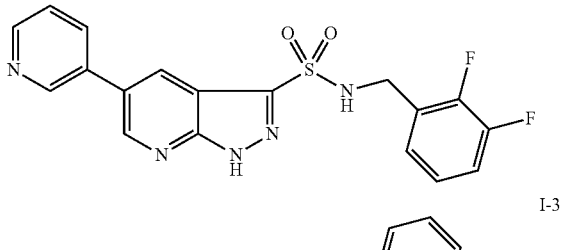
I-2
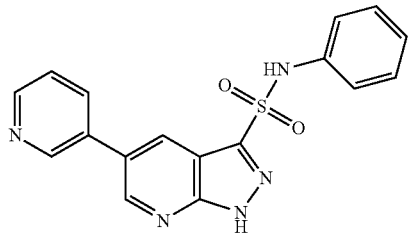
I-3
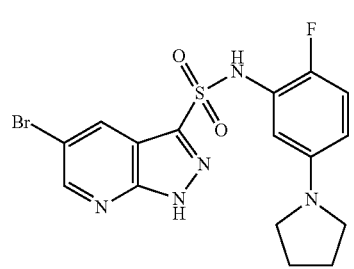
I-4
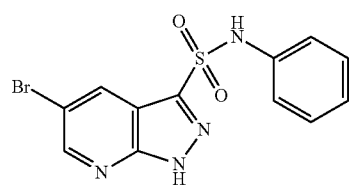
I-5
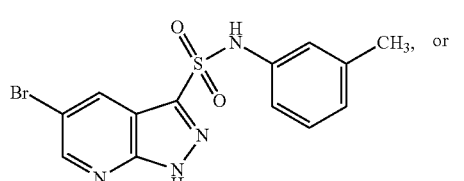
I-6, or
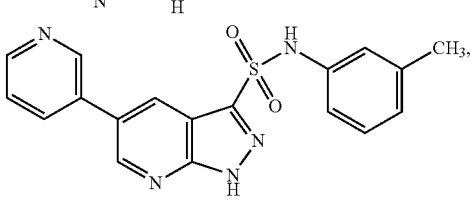
or a pharmaceutically acceptable salt thereof.
2. A compound selected from the following:
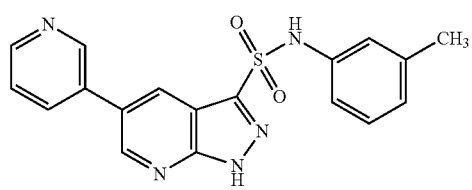
I-7
or a pharmaceutically acceptable salt thereof.
3. A compound selected from the following:
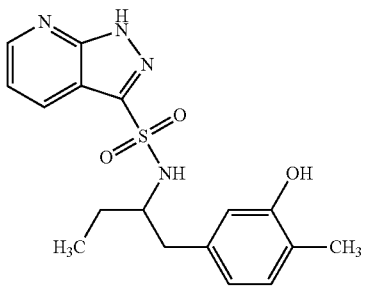
I-16
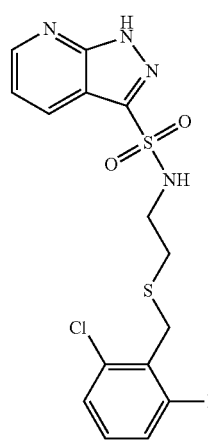
I-22
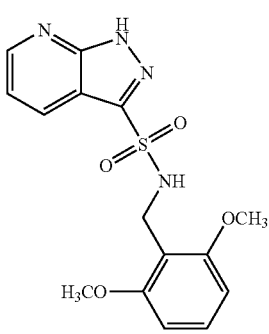
I-23

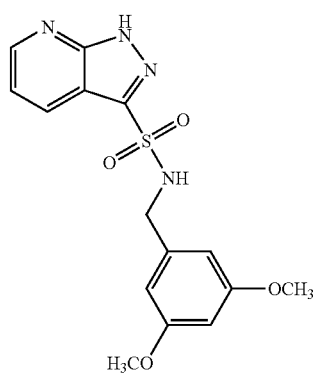 I-24
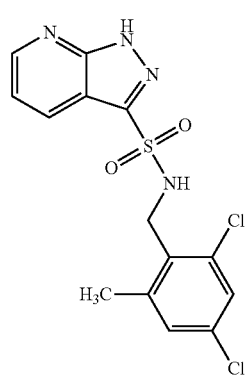 I-25
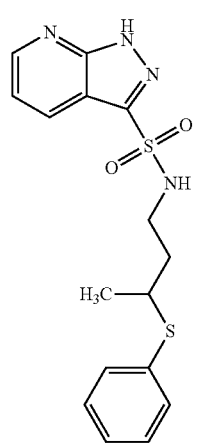 I-32
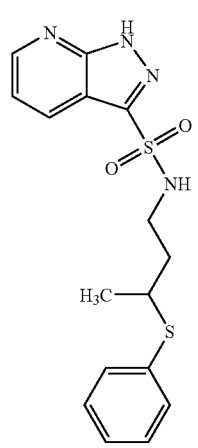 I-32
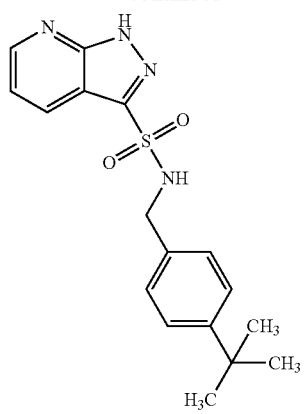 I-35
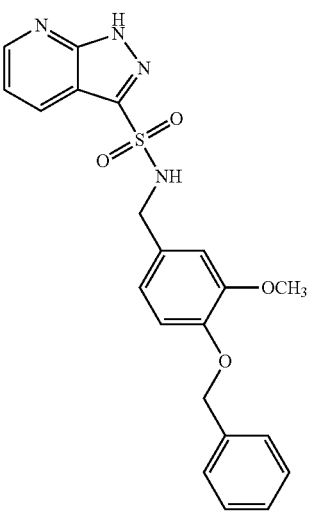 I-37
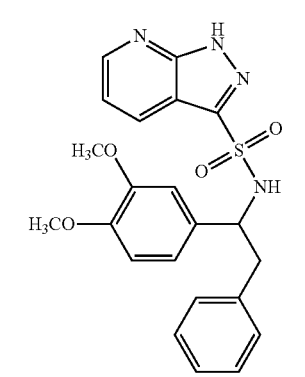 I-40
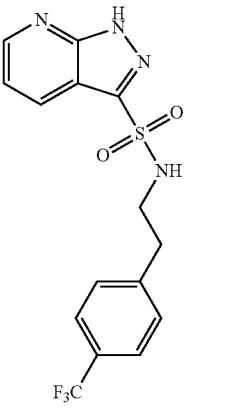 I-44

-continued
I-45
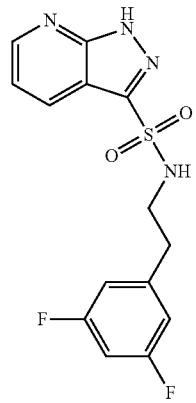
I-48
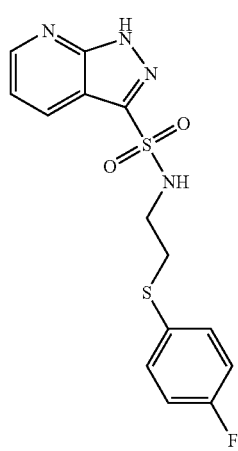
I-49
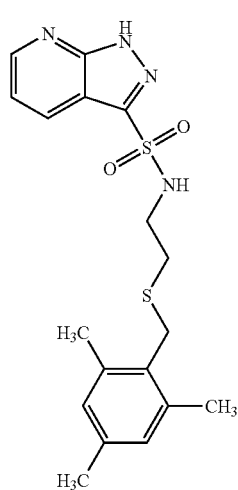
-continued
I-50
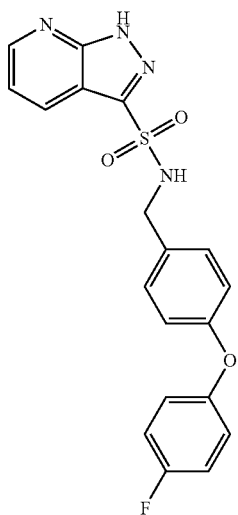
I-53
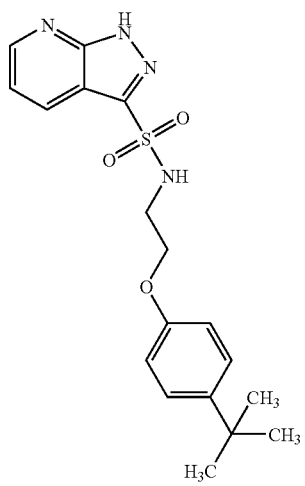
I-54
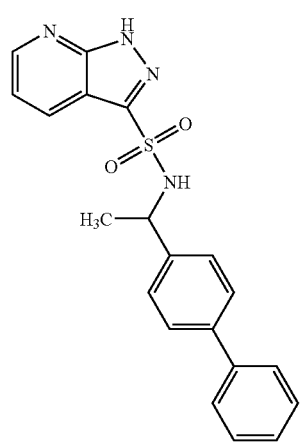

I-60 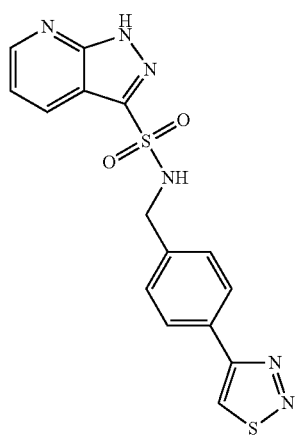
I-61 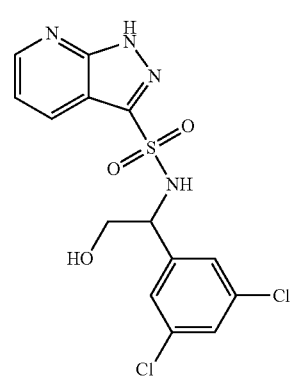
I-63 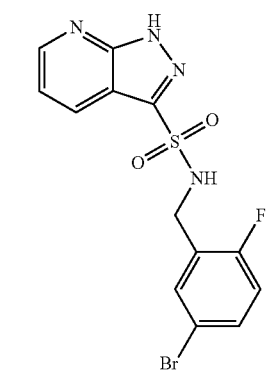
I-68 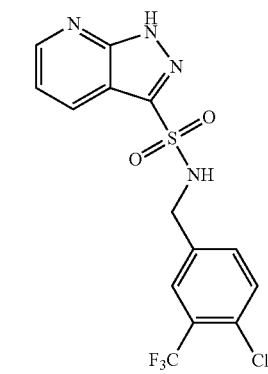
I-81 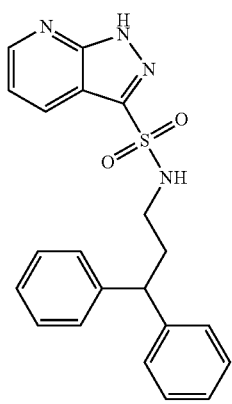
I-82 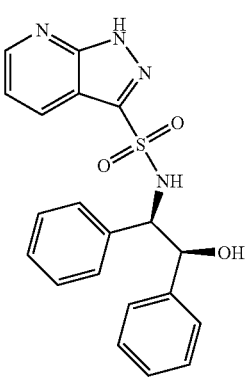
I-83 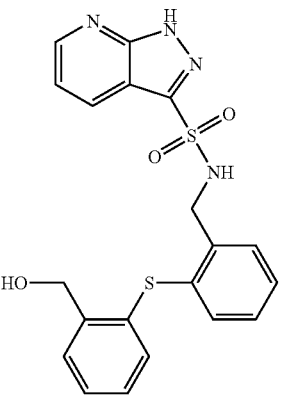
I-84 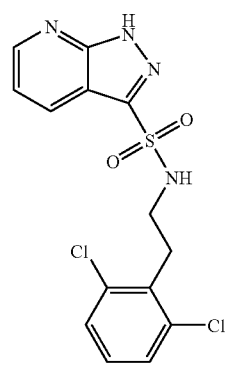

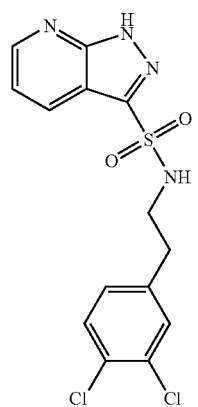 I-85
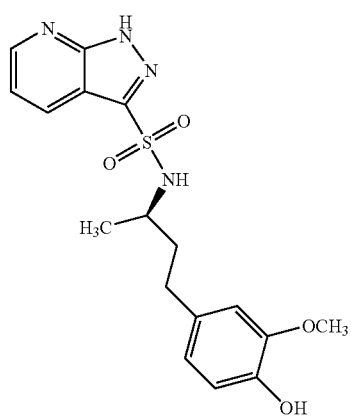 I-89
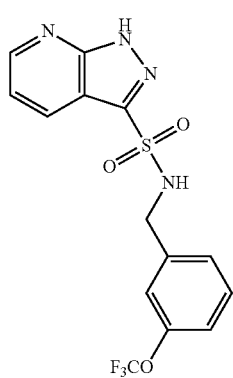 I-86
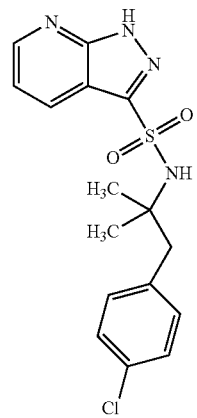 I-91
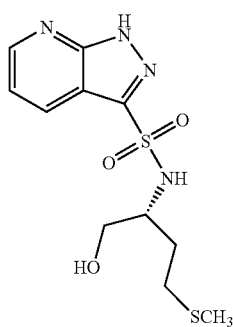 I-87
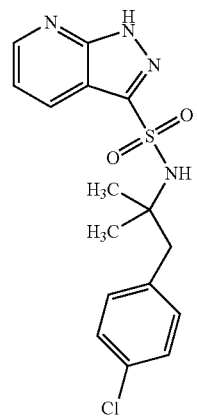 I-91
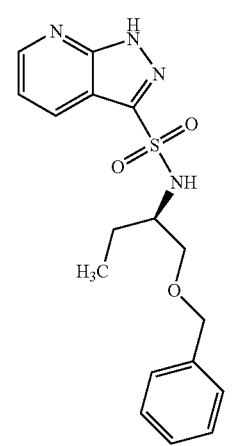 I-88
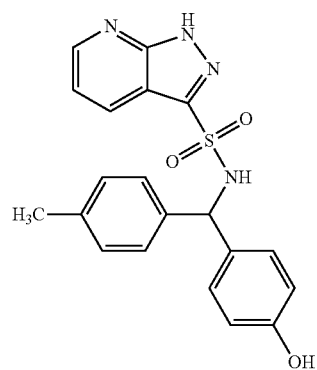 I-92

-continued

I-93

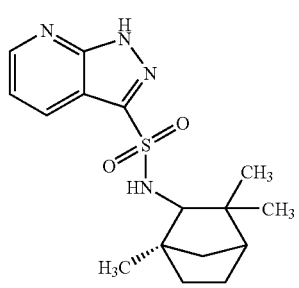

I-95

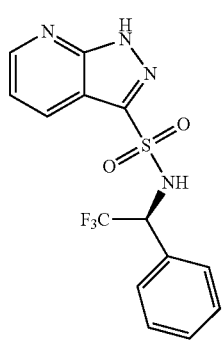

I-103

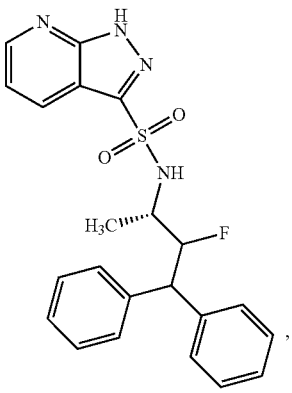

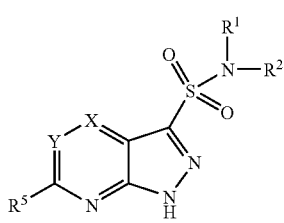

or a pharmaceutically acceptable salt thereof.

4. A composition comprising a compound of any one of claims 1-3, and a pharmaceutically acceptable carrier, adjuvant, or vehicle.

5. A process for preparing a compound of claims 1-3 of formula I:

I

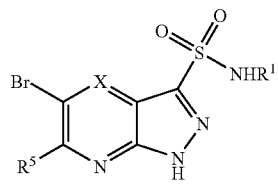

wherein Y is $CR^4$ and $R^1$, $R^2$, X, and $R^5$ are as defined in any one of the compounds of claims 1-3, comprising reacting a compound of formula 6

6

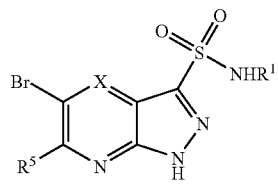

with $R^4$—BA, wherein BA is a suitable boronic acid or ester, under suitable Pd coupling conditions to form the compound of formula I.

6. The process of claim 5, further comprising the step of
a) reacting the compound of formula 4

4

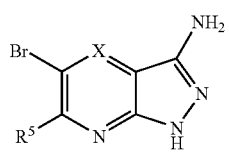

with $NaNO_2$—$H_3O+$, and then with $CuCl_2/SO_2$ to form the desired sulfonyl chloride (formula 5)

5

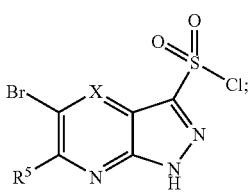

b) reacting the compound of formula 5 with $R^1$—$NH_2$ to form the compound of formula 6.

7. The process of claim 6, further comprising cyclizing the compound of formula 3;

3

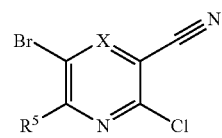

in the presence of hydrazine to form a compound of formula 4.

8. A process for preparing a compound of claims 1-3 of formula I:

I

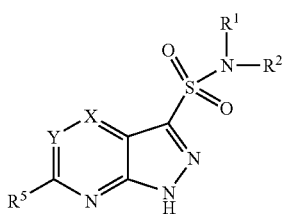

wherein Y is $CR^4$, $R^2$ is H, and $R^1$, X, and $R^5$ are as defined in any one of the compounds of claims 1-3, comprising:
  a) cyclizing a compound of formula 7

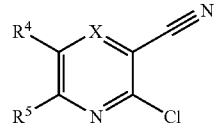
7 in the presence of hydrazine to form a compound of formula 8;

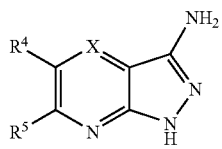
8 b) reacting the compound of formula 8 with $NaNO_2$—$H_3O+$, and then with $CuCl_2/SO_2$ to form the desired sulfonyl chloride of formula 9:

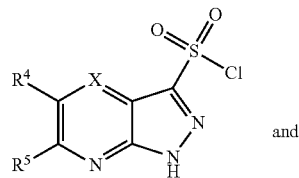
9 and c) reacting a compound of formula 9 with $R^1$—$NH_2$ to form a compound of Formula I wherein $R^1$, $R^4$, and $R^5$ are as defined according to any one of claims 1-3.

* * * * *